US010716298B2

(12) United States Patent
West

(10) Patent No.: US 10,716,298 B2
(45) Date of Patent: Jul. 21, 2020

(54) MATERIALS AND METHODS FOR PRODUCING ANIMALS WITH SHORT HAIR

(71) Applicant: Acceligen, Inc., St. Paul, MN (US)

(72) Inventor: James West, Nashville, TN (US)

(73) Assignee: Acceligen, Inc., Eagan, MN (US)

(*) Notice: Subject to any disclaimer, the term of this patent is extended or adjusted under 35 U.S.C. 154(b) by 0 days.

(21) Appl. No.: 14/862,900

(22) Filed: Sep. 23, 2015

(65) Prior Publication Data

US 2016/0081313 A1 Mar. 24, 2016

Related U.S. Application Data

(60) Provisional application No. 62/054,169, filed on Sep. 23, 2014.

(51) Int. Cl.
C12N 15/00 (2006.01)
C12N 15/63 (2006.01)
C07H 21/02 (2006.01)
C07H 21/04 (2006.01)
A01K 67/027 (2006.01)
C12N 15/85 (2006.01)
C07K 14/72 (2006.01)

(52) U.S. Cl.
CPC .......... A01K 67/0275 (2013.01); C07K 14/72 (2013.01); C12N 15/8509 (2013.01); A01K 2217/072 (2013.01); A01K 2227/10 (2013.01); A01K 2227/101 (2013.01); A01K 2267/02 (2013.01); C07H 21/04 (2013.01); C12N 15/63 (2013.01); C12N 2310/20 (2017.05)

(58) Field of Classification Search
CPC ................ C12N 15/63; C12N 15/8509; C12N 2310/20; C07H 21/02; C07H 21/04
USPC ..................... 435/320.1, 455; 536/23.1, 23.5
See application file for complete search history.

(56) References Cited

U.S. PATENT DOCUMENTS

| | | | |
|---|---|---|---|
| 4,873,191 A | 10/1989 | Wagner et al. |
| 6,169,172 B1 | 1/2001 | Devauchelle et al. |
| 6,548,741 B2 | 4/2003 | DeSousa et al. |
| 6,613,752 B2 | 9/2003 | Kay et al. |
| 7,709,206 B2 | 5/2010 | Denise et al. |
| 8,106,255 B2 | 1/2012 | Carroll et al. |
| 8,518,701 B2 | 8/2013 | Fahrenkrug et al. |
| 8,795,965 B2 | 8/2014 | Zhang |
| 9,528,124 B2 | 12/2016 | Fahrenkrug et al. |
| 2001/0016315 A1 | 8/2001 | Renaville et al. |
| 2005/0003542 A1 | 1/2005 | Kay et al. |
| 2005/0014166 A1 | 1/2005 | Trono et al. |
| 2005/0153317 A1 | 7/2005 | Denise et al. |
| 2010/0251395 A1 | 9/2010 | Harris et al. |
| 2011/0023140 A1 | 1/2011 | Bedell et al. |
| 2011/0023159 A1 | 1/2011 | Bedell et al. |
| 2011/0059160 A1 | 3/2011 | Essner et al. |
| 2011/0281306 A1 | 11/2011 | Kim et al. |
| 2012/0192298 A1 | 7/2012 | Weinstein et al. |
| 2012/0222143 A1 | 8/2012 | Fahrenkrug et al. |
| 2013/0117870 A1 | 5/2013 | Fahrenkrug et al. |
| 2015/0067898 A1 | 3/2015 | Fahrenkrug et al. |
| 2015/0156996 A1 | 6/2015 | Fahrenkrug et al. |
| 2016/0029604 A1 | 2/2016 | Fahrenkrug et al. |
| 2016/0262360 A1 | 9/2016 | Littlejohn |
| 2017/0079251 A1 | 3/2017 | Songstegard et al. |
| 2018/0051298 A1 | 2/2018 | Fahrenkrug et al. |
| 2019/0194687 A1* | 6/2019 | Fahrenkrug et al. |
| 2019/0223417 A1 | 7/2019 | Sonstegard et al. |

FOREIGN PATENT DOCUMENTS

| | | |
|---|---|---|
| JP | 2009/225807 A | 10/2009 |
| WO | 2015060732 A1 | 4/2015 |
| WO | WO-2015168125 A1 | 11/2015 |
| WO | WO-2016049182 A1 | 3/2016 |
| WO | 2017053315 A1 | 3/2017 |
| WO | WO-2017053315 A1 | 3/2017 |

OTHER PUBLICATIONS

Shinobara et al., 2007, Transgenic research, vol. 16, p. 333-339.*
Houdebine, Louis-Marie, 2007, Methods in Molecular Biology, vol. 360, p. 163-202.*
Carstea et al., 2009, World Journals of Stem Cells, vol. 1, No. 1, p. 22-29.*
Patil et al., 2011, Indian Journal of Public Health research & Development, vol. 2, No. 1, p. 106-109.*
Khodarovich et al., 2013, Applied Biochemistry and Microbiology, vol. 49, No. 9, pp. 711-722.*
Selsby et al., 2015, ILAR Journal, vol. 56, No. 1, p. 116-126.*
Maksimenko et al., 2013, Acta Naturae, vol. 5, No. 1, p. 33-46.*
Pandey, Prativa, 2007, Abstracts, 59th Southeast regional Meeting of the American Chemical Society, Greenville, SC, United States, GEN-671, Publisher: American Chemical Society, Washington D.C.*
Bryan et al., 2013, http://www.elsevierblogs.com/currentcomments/? p=962, Implications of protein fold switching, p. 1-4.*
Maqbool et al., 2015, Biochemical Society Transactions, vol. 43, No. 5, p. 1011-1017.*
Guo et al., 2015, Cell Research, vol. 25, p. 767-768.*
Lee et al., 2016, Drug Discovery Today: Disease Models, vol. 20, p. 13-20.*
Craven, A.J. et al., "Prolactin Signaling Influences the Timing Mechanism of the Hair Follicle: Analysis of Hair Growth Cycles in Prolactin Receptor Knockout Mice," Endocrinology, Jun. 2001, 142(6):2533-9.
NCBI, GenBank accession No. AAA51417.1, Oct. 30, 1994.

(Continued)

Primary Examiner — Shin Lin Chen
(74) Attorney, Agent, or Firm — Wilson Sonsini Goodrich & Rosati

(57) ABSTRACT

The subject invention provides materials and methods for producing animals with short hair length. In a preferred embodiment, this is accomplished by altering in the animal the nucleotide sequence that encodes the prolactin receptor (PRLR) protein such that a truncated version of the protein is produced. Advantageously, and surprisingly, the truncated protein produced according to the subject invention retains lactogenic functionality, but causes the animal to have a short-hair coat.

5 Claims, 1 Drawing Sheet

Specification includes a Sequence Listing.

(56) References Cited

OTHER PUBLICATIONS

Olson, T.A. et al., "Evidence of a major gene influencing hair length and heat tolerance in *Bos taurus* cattle," *J Anim Sci.*, Jan. 2003, 81(1):80-90.

Sonstegard, T.S. et al., "The identification of a putative mutation for SLICK hair coat in Senepol cattle," *Joint Annual Meeting*, Jul. 20-24, 2014, Kansas City, Missouri, USA, Abstract.

Davis, S.R., et al., "Breeding and Genetics Symposium: Breeding heat tolerant dairy cattle: the case for introgression of the "slick" prolactin receptor variant into Bos taurus dairy breeds." J. Anim. Sci., 2017, 95: 1788-1800.

Huang, Kuang-tzu, "Studies on Truncated Isoforms of the Prolactin Receptors. A Dissertation submitted in partial satisfaction of the requirement for the degree of Doctor of Philosophy in Biomedical Sciences." ProQuest Dissertations & Theses Global: The Sciences and Engineering Collection, 2000, pp. 1-144.

Littlejohn, M.D., et al., "Functionally reciprocal mutations of the prolactin signalling pathway define hairy and slick cattle." Nature Communications, Dec. 2014, 5: 1-8.

Porto-Neto, L.R., et al., "Convergent Evolution of Slick Coat in Cattle through Truncation Mutations in the Prolactin Receptor." Frontiers in Genetics, Feb. 2018, 9(57): 1-8.

Heo et al., "CRISPR/Cas9 Nuclease-Mediated Gene Knock-Inin Bovine-Induced Pluripotent Cells," Stem Cells and Development, 2015, 24(3):393-402.

EP15844824.1 Extended European Search Report dated Apr. 23, 2018.

EP16849434.2 Extended European Search Report dated Jan. 25, 2019.

U.S. Appl. No. 15/270,901 Office Action dated Sep. 21, 2018.

Altschul et al. Basic local alignment search tool. J Mol Biol 215(3):403-410 (1990).

Bagle et al. Transgenic Animals and their Application in Medicine. International Journal of Medical Research & Health Sciences. 2(1):107-116 (2012).

Bignon et al. Long and short forms of the ovine prolactin receptor: cDNA cloning and genomic analysis reveal that the two forms arise by different alternative splicing mechanisms in ruminants and in rodents. Journal of Molecular Endocrinology 19:109-120 (1997).

Branda et al., Talking About a Revolution: The Impact of Site-Specific Recombinases on Genetic Analyses in Mice. Developmental Cell, 6.1 (Jan. 2004): 7-28.

Brooks., Molecular Mechanisms of Prolactin and It's Receptor. Endocrine Reviews, 33.4 (Aug. 2012): 504-525.

Burrow. Variances and covariances between productive and adaptive traits and temperament in a composite breed of tropical beef cattle. Livestock Production Science 70(3):213-233 (Aug. 2001). DOI: https://doi.org/10.1016/S0301-6226(01)00178-6.

Cibelli, et al. Cloned transgenic calves produced from nonquiescent fetal fibroblasts. Science, 280 (1998):1256-1258.

Cogoni et al., Gene Silencing in Neurospora crassa Requires a Protein Homologous to RNA-Dependent RNA Polymerase. Nature 399 (May 13, 1999): 166-169.

Cogoni et al., Transgene Silencing of the al-1 Gene in Vegetative Cells of Neurospora in Mediated by a Cytoplasmic Effector and Does Not Depend on DNA-DNA interactions or DNA Methylation. The EMBO Journal. 15.12 (1996): 3153-3163.

Cong, et al. Multiplex genome engineering using CRISPR/Cas systems. Science. 339.6121 (Feb. 15, 2013): 819-23. doi: 10.1126/science.1231143. Epub Jan. 3, 2013.

Dieffenbach, et al. PCR Primer: A Laboratory Manual, ed. Cold Spring Harbor Laboratory Press, 1995.

Dikmen et al. The SLICK hair locus derived from Senepol cattle confers thermotolerance to intensively managed lactating Holstein cows. J. Dairy Sci. 97:5508-5520.

Dupuy et al., Mammalian Germ-Line Transgenesis by Transposition Proceeding of the National Academy of Sciences, 99.7 (2002): 4495-4499.

Fire et al. Potent and specific genetic interference by double-stranded RNA in Caenorhabditis elegans. Nature 391 (1998): 806-811.

Gish et al. Identification of protein coding regions by database similarity search. Nature Genetics 3:266-272 (1993).

Guatelli et al. Isothermal, in vitro amplification of nucleic acids by a multienzyme reaction modeled after retroviral replication. PNAS USA 87(5):1874-1878 (1990).

Hammond et al. Heat tolerance in Tuli-, Senepol-, and Brahman-sired F1 Angus heifers in Florida. Journal of Animal Science 76(6):1568-1577 (Jun. 1, 1998). DOI: https://doi.org/10.2527/1998.7661568x.

Hammond et al. Heat tolerance in two tropically adapted Bos taurus breeds, Senepol and Romosinuano, compared with Brahman, Angus, and Hereford cattle in Florida. Journal of Animal Science 74(2):295-303 (Feb. 1, 1996). DOI: https://doi.org/10.2527/1996.742295x.

Higgins et al. [22] Using CLUSTAL for multiple sequence alignments. Methods Enzymol 266:383-402 (1994). DOI: https://doi.org/10.1016/S0076-6879(96)66024-8.

Huson et al., Genome-wide Association Study and Ancestral Origins of the Slick-Hair Coat in Tropically Adapted Cattle. Genetics, 5 (Apr. 2014): 1-12.

International search report with written opinion dated Dec. 19, 2016 for PCT/US2016/052693.

Katsuyama et al. An efficient strategy for TALEN-mediated genome engineering in *Drosophila*. Nucleic Acids Research 41(17):e163 (Sep. 1, 2013). Epub Jul. 22, 2013. DOI: https://doi.org/10.1093/nar/gkt638. 9 pages.

Kawakami, Tol2: a versatile gene transfer vector in vertebrates. Genome Biology, 8(suppl 1) article s7, S7.1-S7.10 (2007).

Kennerdell et al., Use of dsRNA-Mediated Genetic Interference to Demonstrate that frizzled and frizzled 2 Act in the Wingless Pathway. Cell, 95 (Dec. 23, 1998): 1017-1026.

Kiwaki et al., Correction of Ornithine Transcarbamylase Deficiency in Adult spfash Mice and in OTC-Deficient Human Hepatocytes with Recombinant Adenoviruses Bearing the CAG Promoter. Human Gene Therapy, 7 (May 1, 1996): 821-830.

Lavitrano et al., Efficient Production by Sperm-Mediated Gene Transfer of Human Decay Accelerating Factor (hDAF) Transgenic Pigs for Xenotransplantation, Proceedings of the National Academy of Science, 99.22 (Oct. 29, 2002): 14230-14235.

Lavitrano et al., Sperm-Mediated Gene Transfer, Reproduction, Fertility and Development, 18 (2006): 19-23.

Lewis. PCR's Competitors are alive and well and moving rapidly towards commercialization. Genetic Engineering News, 12.1 (1992): 2 pages.

Lo. Transformation by iontophoretic microinjection of DNA: multiple integrations without tandem insertions. Mol. Cell. Biol., 3.10 (1983): 1803-1814.

Loi et al. Synergies between assisted reproduction technologies and functional genomics. Genet Sel Evol 48:53 (2016). 7 pages.

Lu et al., TALEN-Mediated Gene Mutagenesis In Rhesus And Cynomolgus Monkeys. Cell Stem Cell, 14.3 (Mar. 6, 2014): 323-328.

MacKinnon et al. Genetic variation and covariation for growth, parasite resistance and heat tolerance in tropical cattle. Livestock Production Science 27(2-3):105-122 (Feb. 1991). DOI: https://doi.org/10.1016/0301-6226(91)90090-D.

Mariasegaram et al. The slick hair coat locus maps to chromosome 20 in Senepol-derived cattle. Anim Genet 38(1):54-59 (Feb. 2007). doi:10.1111/j.1365-2052.2007.01560.x.

McIntyre et al., Design and Cloning Strategies for Constructing shRNA Expression Vectors. BMC Biotechnology, 6.1 (Jan. 5, 2006): 8 Pages.

Miao et al. Recent Advances and Applications of Transgenic Animal Technology. IntechOpen (May 30, 2012). DOI: 10.5772/38040. 30 pages.

Miskey et al., The Ancient Mariner Sails Again: Transposition of the Human Hsmarl Element by a Reconstructed Transposase and Activities of the SETMAR Protein on Transposon Ends. Molecular and Cellular Biology, 27.12 (Jun. 2007): 4589-4600.

Miskey et al., The Frog Prince: a reconstructed transposon from Rana pipiens with high transpositional activity in vertebrate cells. Nucleic Acids Res. 31.23 (2003): 6873-6881.

(56) References Cited

OTHER PUBLICATIONS

Misquitta et al, Targeted Disruption of Gene Function in *Drosophila* by RNA Interference (RNA-i): A Role for Nautilus in Embryonic Somatic Muscle Formation. Proceedings of the National Academy of Science, 96 (Feb. 1999): 1451-1456.
Orban et al., Tissue and Site-Specific DNA Recombination in Transgenic Mice. Proceedings of the National Academy of Science, 89 (Aug. 1992): 6861-6865.
Pavlopoulos et al., The DNA transposon Minos as a tool for transgenesis and functional genomic analysis in vertebrates and invertebrates. Genome biology 8.1 (suppl 1) article S2 (2007): S2.1-S2.7.
PCT/US2015/051717 International Preliminary Report on Patentability dated Mar. 28, 2017.
PCT/US2015/051717 International Search Report and Written Opinion dated Dec. 30, 2015.
PCT/US2016/052693 International Preliminary Report on Patentability dated Mar. 27, 2018.
Pearson et al. Improved tools for biological sequence comparison. PNAS USA 85(8):2444-2448 (1988).
Pezet et al., Tyrosine Docking Sites Of The Rat Prolactin Receptor Required For Association And Activation Of 3tat5. Journal Of Biological Chemistry, 272.40 (Oct. 3, 1997): 25043-25050.
Romano et al, Quelling: transient inactivation of gene expression in Neurospora crassa by transformation with homologous sequences. Mol. Microbiol., 6.22 (1992): 3343-3353.
Sonstegard, Discovery of Convergent Adaptation that Alleviate Heat Stress in Taurine Cattle. Cattle and Swine Workshop in the Plant and Animal Genome XXIII meeting (Jan. 13-17, 2015).
Sonstegard, Identification of a Putative Mutation for SLICK Hair Coat in Senepol Cattle. Breeding and Genetics: Applications and Methods in Animal Breeding (Joint Annual Meeting) (Jul. 23, 2014).
Sonstegard, The Identification of the Mutation for SLICK Hair Coat in Senepol Cattle—An Adaptive Variant with Effects on Thermotolerance and Milk Production. Ruminant Genetics and Genomics Workshop. Jul. 29, 2014.
Tchelet et al. Extracellular domain of prolactin receptor from bovine mammary gland: expression in *Escherichia coli*, purification and characterization of its interaction with lactogenic hormones. Journal of Endocrinology 144:393-403 (1995).
Thompson, et al. CLUSTAL W: improving the sensitivity of progressive multiple sequence alignment through sequence weighting, position-specific gap penalties and weight matrix choice. Nucleic Acids Res. Nov. 11, 1994;22(22):4673-80.
Thompson, et al. Germ line transmission and expression of a corrected HPRT gene produced by gene targeting in embryonic stem cells. Cell, 56 (1989):313-321.
Turner. Genetic variation of rectal temperature in cows and its relationship to fertility. Animal Science 35(3):401-412 (Dec. 1982). DOI: https://doi.org/10.1017/S0003356100001094.
Turner. Variation in rectal temperature of cattle in a tropical environment and its relation to growth rate. Animal Science 38(1):417-427 (Jun. 1984). DOI: https://doi.org/10.1017/S0003356100041611.
U.S. Appl. No. 14/625,797 Non-Final Office Action dated May 10, 2017.
U.S. Appl. No. 15/270,901 Non-Final Office Action dated Feb. 22, 2018.
Van Der Putten, et al. Efficient insertion of genes into the mouse germ line via retroviral vectors. Proc. Natl. Acad. Sci. USA, 82 (1985): 6148-1652.
Visscher et al., Breeding Objectives for Pasture Based Dairy Production Systems. Livestock Production Science, 40 (1994): 123-137.
Wakayama, et al. Full-term development of mice from enucleated oocytes injected with cumulus cell nuclei. Nature, 394 (1998): 369-374.
Weiss. Hot prospect for new gene amplifier. Science, 254 (1991): 1292-1293.
Wilmut, et al. Viable offspring derived from fetal and adult mammalian cells. Nature, 385 (1997): 810-813.
Xu et al., CMV-β-Actin Promoter Directs Higher Expression from an Adeno-Associated Viral Vector in the Liver than the Cytomegalovirus or Elongation Factor 1α Promoter and Results in Therapeutic Levels of Human Factor X in Mice, Hum Gene Ther., 12 (2001): 563-573.
Zu et al. TALEN-mediated precise genome modification by homologous recombination in zebrafish. Nature Methods, vol. 10, pp. 329-331 (2013). Epub Feb. 24, 2013.
Hammond et al. Rectal temperature and grazing time in selected beef cattle breeds under tropical summer conditions in subtropical Florida. Tropical Agriculture (Trinidad and Tobago). (Apr. 1994). v. 71(2) p. 128-134.
EP15844824.1 Office Action dated Nov. 29, 2019.

\* cited by examiner

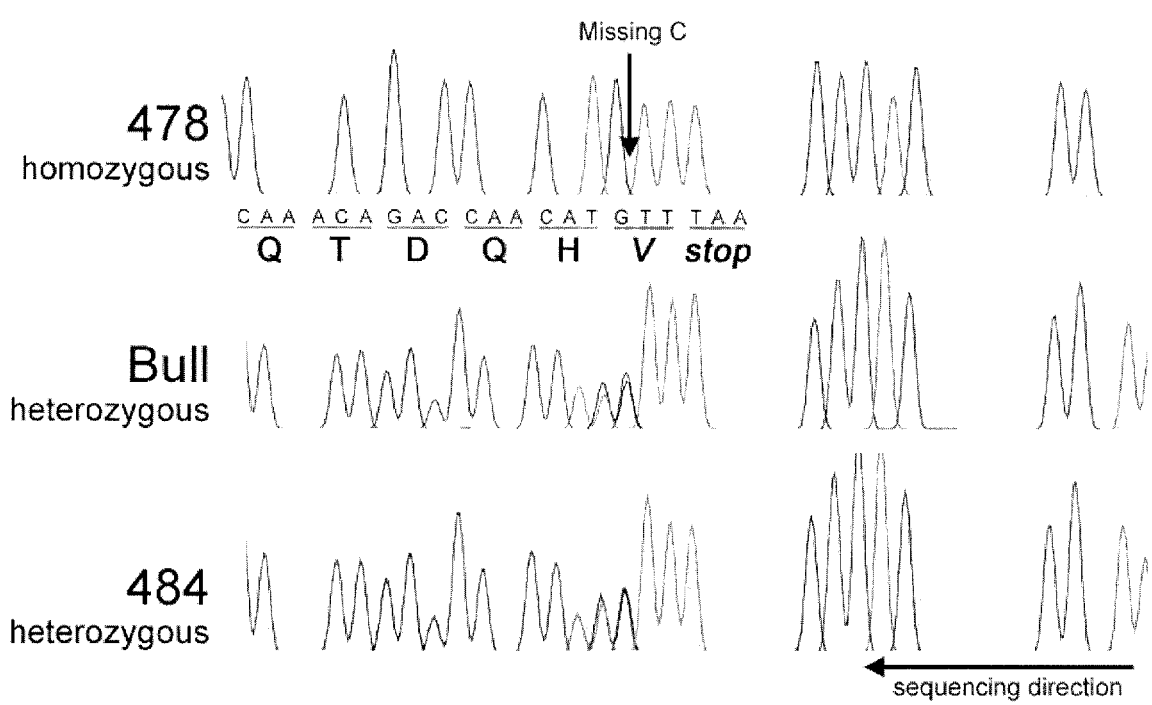

SEQUENCE LISTING

<160> NUMBER OF SEQ ID NOS: 13

<210> SEQ ID NO 1
<211> LENGTH: 2389
<212> TYPE: DNA
<213> ORGANISM: Bos taurus

<400> SEQUENCE: 1

```
cgggcaaatg ctgaggatac tttccaagtg aaccctgagt gaacctctaa tatatttatt    60
tcctgtggaa agaggaagga gccaacatga aggaaaatgc agcatctaga gtggttttca   120
ttttgctact ttttctcagt gtcagccttc tgaatggaca gtcacctcct gaaaaaccca   180
agctcgttaa atgtcggtct cctggaaagg aaacattcac ctgctggtgg gagcctgggg   240
cagatggagg acttcctacc aattacacgc tgacttacca caaggaagga gaaacactca   300
tccatgaatg tccagactac aaaaccgggg gccccaactc ctgctacttt agcaagaagc   360
acacctccat atgaagatg tacgtcatca cagtaaacgc catcaaccag atgggaatca   420
gttcctcgga tccactttat gtgcacgtga cttacatagt tgaaccagag cctcctgcaa   480
acctgacttt ggaattaaaa catccagaag atagaaaacc atatctatgg ataaaatggt   540
ctccacccac catgactgat gtaaaatctg gttggttcat tatccagtac gaaattcgat   600
taaaacctga aaagcaact gattgggaga ctcattttac tctgaagcaa actcagctta   660
agattttcaa cttatatcca ggacaaaaat accttgtgca gattcgctgc aagccagacc   720
atggatactg gagtgagtgg agcccagaga gctccatcca gatacctaat gacttcccag   780
tgaaggacac aagcatgtgg atctttgtgg ccatcctttc tgctgtcatc tgtttgatta   840
tggtctgggc agtggctttg aagggctata gcatggtgac ctgcatcctc ccaccagttc   900
cagggccaaa aataaaagga tttgatgttc atctgctgga aagggcaag tccgaagaac   960
ttctgcgagc tctggaaagc caagacttcc ccccacttc tgactgcgag acttgctga  1020
tggagttcat agaggtagat gactgtgagg accagcagct gatgccacgc ccctccaaag  1080
aacacacgga gcaaggcgtg aagcccatgc acctggatct tgacagtgac tctggccggg  1140
gcagctgcga cagcccttcg ctcttgtctg aaaagtgtga tgaacctcag gcccatccct  1200
ccaagttcca tactcccgag ggccctgaga agctggagaa tccggaaaca aaccttacat  1260
gtctccaggc ccctcagagc acaagcgtgg aaggcaaaat cccctatttt ctggccaatg  1320
gacccaaatc ttccacatgg cctttcccgc agccccccag cctatacagc cccagatatt  1380
cttaccacaa cattgctgac gtgtgtgagc tggcctggg catggccggc accacagcca  1440
cttcgctgga ccaaacagac caacatgctt taaaagcctc aaaaaccatt gaaactggca  1500
gggaaggaaa ggcaaccaag cagagggagt cagaaggctg cagttccaag cctgaccaag  1560
acacggtgtg gccacgaccc caagacaaaa ccccttgat ctctgctaaa cccttggaat  1620
acgtggagat ccacaaggtc agccaagatg gagtgctggc tctgttccca aaacaaaacg  1680
agaagtttgg cgcccctgaa gccagcaagg agtactcaaa ggtgtcccgg gtgacagata  1740
gcaacatcct ggtattggtg ccggatccgc aagcgcaaaa cctgactctg ttagaagaac  1800
cagccaagaa ggccccgcca gccctgccat agaatccagc caaggccgac ctggctatct  1860
cccccacaac cccaggcaac tgcagactcc agttgggctg gggactgggt cccgcaggtt  1920
ttatgcactc ttgcagtgag agttatggaa ggatgggttc aattgtgatt ttccttcagg  1980
gaacactaca gagtacgtga aatgcactct accagagagg gctcaagaac agggttagaa  2040
tgacactacc caactcccag ttcactctta attctctatt ttcaaccagt tgcctctttg  2100
tccaacagct gattccagaa caaatcgttc catcttgtgt gatttgtaga tttacttttt  2160
tgctattagt tgtcagatta tatgttcaaa gatataaaag cacattgcct agtattctta  2220
agagacagtg ccaataggta tataatctgg aaaaggcctt catggtttcg tatgtgacag  2280
```

| | |
|---|---:|
| agggggtataa gtcagtcaaa attgtttacc atgggaagat ggtagatagg agagaaatgc | 2340 |
| catgaaaacc actttgaaga ccagttgctt aacctttgca ctcctctttt | 2389 |

<210> SEQ ID NO 2
<211> LENGTH: 1746
<212> TYPE: DNA
<213> ORGANISM: Bos taurus

<400> SEQUENCE: 2

| | |
|---|---:|
| atgaaggaaa atgcagcatc tagagtggtt ttcattttgc tacttttttct cagtgtcagc | 60 |
| cttctgaatg dacagtcacc tcctgaaaaa cccaagctcg ttaaatgtcg gtctcctgga | 120 |
| aaggaaacat tcacctgctg gtgggagcct ggggcagatg gaggacttcc taccaattac | 180 |
| acgctgactt accacaagga aggagaaaca ctcatccatg aatgtccaga ctacaaaacc | 240 |
| gggggcccca actcctgcta cttttagcaag aagcacacct ccatatggaa gatgtacgtc | 300 |
| atcacagtaa acgccatcaa ccagatggga atcagttcct cggatccact ttatgtgcac | 360 |
| gtgacttaca tagttgaacc agagcctcct gcaaacctga ctttggaatt aaaacatcca | 420 |
| gaagatagaa aaccatatct atggataaaa tggtctccac ccaccatgac tgatgtaaaa | 480 |
| tctggttggt tcattatcca gtacgaaatt cgattaaaac ctgagaaagc aactgattgg | 540 |
| gagactcatt ttactctgaa gcaaactcag cttaagattt tcaacttata tccaggacaa | 600 |
| aaatacctttg tgcagattcg ctgcaagcca gaccatggat actggagtga gtggagccca | 660 |
| gagagctcca tccagatacc taatgacttc ccagtgaagg acacaagcat gtggatcttt | 720 |
| gtggccatcc tttctgctgt catctgtttg attatggtct gggcagtggc tttgaagggc | 780 |
| tatagcatgg tgacctgcat cctcccacca gttccagggc caaaaataaa aggatttgat | 840 |
| gttcatctgc tggagaaggg caagtccgaa gaacttctgc gagctctgga agccaagac | 900 |
| ttcccccccca cttctgactg cgaggacttg ctgatggagt tcatagaggt agatgactgt | 960 |
| gaggaccagc agctgatgcc acgcccctcc aaagaacaca cggagcaagg cgtgaagccc | 1020 |
| atgcacctgg atcttgacag tgactctggc cggggcagct gcgacagccc ttcgctcttg | 1080 |
| tctgaaaagt gtgatgaacc tcaggccat ccctccaagt tccatactcc cgagggcct | 1140 |
| gagaagctgg agaatccgga acaaaacctt acatgtctcc aggcccctca gagcacaagc | 1200 |
| gtggaaggca aaatccccta ttttctggcc aatggaccca atcttccac atggcctttc | 1260 |
| ccgcagcccc ccagcctata cagccccaga tattcttacc acaacattgc tgacgtgtgt | 1320 |
| gagctggccc tgggcatggc cggcaccaca gccacttcgc tggaccaaac agaccaacat | 1380 |
| gcttttaaaag cctcaaaaac cattgaaact ggcagggaag gaaaggcaac caagcagagg | 1440 |
| gagtcagaag gctgcagttc caagcctgac caagacacgg tgtggccacg accccaagac | 1500 |
| aaaaccccct tgatctctgc taaacccttg gaatacgtgg agatccacaa ggtcagccaa | 1560 |
| gatggagtgc tggctctgtt cccaaaacaa aacgagaagt ttggcgcccc tgaagccagc | 1620 |
| aaggagtact caaaggtgtc ccgggtgaca gatagcaaca tcctggtatt ggtgccggat | 1680 |
| ccgcaagcgc aaaacctgac tctgttagaa gaaccagcca agaaggcccc gccagccctg | 1740 |
| ccatag | 1746 |

<210> SEQ ID NO 3
<211> LENGTH: 1170
<212> TYPE: DNA
<213> ORGANISM: Bos taurus

<400> SEQUENCE: 3

```
atgaaggaaa atgcagcatc tagagtggtt ttcattttgc tacttttttct cagtgtcagc      60 cttctgaatg gacagtcacc tcctgaaaaa cccaagctcg ttaaatgtcg gtctcctgga     120
aaggaaacat tcacctgctg gtgggagcct ggggcagatg gaggacttcc taccaattac     180
acgctgactt accacaagga aggagaaaca ctcatccatg aatgtccaga ctacaaaacc     240
gggggcccca actcctgcta ctttagcaag aagcacacct ccatatggaa gatgtacgtc     300
atcacagtaa acgccatcaa ccagatggga atcagttcct cggatccact ttatgtgcac     360
gtgacttaca tagttgaacc agagcctcct gcaaacctga ctttggaatt aaaacatcca     420
gaagatagaa aaccatatct atggataaaa tggtctccac ccaccatgac tgatgtaaaa     480
tctggttggt tcattatcca gtacgaaatt cgattaaaac ctgagaaagc aactgattgg     540
gagactcatt ttactctgaa gcaaactcag cttaagattt tcaacttata tccaggacaa     600
aaataccttg tgcagattcg ctgcaagcca gaccatggat actggagtga gtggagccca     660
gagagctcca tccagatacc taatgacttc ccagtgaagg acacaagcat gtggatcttt     720
gtggccatcc tttctgctgt catctgtttg attatggtct gggcagtggc tttgaagggc     780
tatagcatgg tgacctgcat cctcccacca gttccagggc caaaaataaa aggatttgat     840
gttcatctgc tggagaaggg caagtccgaa gaacttctgc gagctctgga aagccaagac     900
ttccccccca cttctgactg cgaggacttg ctgatggagt tcatagaggt agatgactgt     960
gaggaccagc agctgatgcc acgccctcc aaagaacaca cggagcaagg cgtgaagccc    1020
atgcacctgg atcttgacag tgactctggc cggggcagct gcgacagccc ttcgctcttg    1080
tctgaaaagt gtgatgaacc tcaggcccat ccctccaagt tccatactcc cgagggccct    1140
gagaagctgg agaatccgga aacaaacctt                                      1170
```

<210> SEQ ID NO 4
<211> LENGTH: 1383
<212> TYPE: DNA
<213> ORGANISM: Bos taurus

<400> SEQUENCE: 4

```
atgaaggaaa atgcagcatc tagagtggtt ttcattttgc tacttttttct cagtgtcagc      60 cttctgaatg gacagtcacc tcctgaaaaa cccaagctcg ttaaatgtcg gtctcctgga     120
aaggaaacat tcacctgctg gtgggagcct ggggcagatg gaggacttcc taccaattac     180
acgctgactt accacaagga aggagaaaca ctcatccatg aatgtccaga ctacaaaacc     240
gggggcccca actcctgcta ctttagcaag aagcacacct ccatatggaa gatgtacgtc     300
atcacagtaa acgccatcaa ccagatggga atcagttcct cggatccact ttatgtgcac     360
gtgacttaca tagttgaacc agagcctcct gcaaacctga ctttggaatt aaaacatcca     420
gaagatagaa aaccatatct atggataaaa tggtctccac ccaccatgac tgatgtaaaa     480
tctggttggt tcattatcca gtacgaaatt cgattaaaac ctgagaaagc aactgattgg     540
gagactcatt ttactctgaa gcaaactcag cttaagattt tcaacttata tccaggacaa     600
aaataccttg tgcagattcg ctgcaagcca gaccatggat actggagtga gtggagccca     660
gagagctcca tccagatacc taatgacttc ccagtgaagg acacaagcat gtggatcttt     720
gtggccatcc tttctgctgt catctgtttg attatggtct gggcagtggc tttgaagggc     780
tatagcatgg tgacctgcat cctcccacca gttccagggc caaaaataaa aggatttgat     840
gttcatctgc tggagaaggg caagtccgaa gaacttctgc gagctctgga aagccaagac     900
```

```
ttcccccca cttctgactg cgaggacttg ctgatggagt tcatagaggt agatgactgt      960
gaggaccagc agctgatgcc acgcccctcc aaagaacaca cggagcaagg cgtgaagccc     1020
atgcacctgg atcttgacag tgactctggc cggggcagct gcgacagccc ttcgctcttg     1080
tctgaaaagt gtgatgaacc tcaggcccat ccctccaagt tccatactcc cgagggccct     1140
gagaagctgg agaatccgga acaaaacctt acatgtctcc aggcccctca gagcacaagc     1200
gtggaaggca aaatccccta ttttctggcc aatggaccca atcttccac atggcctttc      1260 ccgcagcccc ccagcctata cagccccaga tattcttacc acaacattgc tgacgtgtgt     1320
gagctggccc tgggcatggc cggcaccaca gccacttcgc tggaccaaac agaccaacat     1380
gtt                                                                  1383

<210> SEQ ID NO 5
<211> LENGTH: 1383
<212> TYPE: DNA
<213> ORGANISM: Bos taurus

<400> SEQUENCE: 5
atgaaggaaa atgcagcatc tagagtggtt ttcattttgc tacttttct cagtgtcagc       60 cttctgaatg gacagtcacc tcctgaaaaa cccaagctcg ttaaatgtcg gtctcctgga     120
aaggaaacat tcacctgctg gtgggagcct ggggcagatg gaggacttcc taccaattac     180
acgctgactt accacaagga aggagaaaca ctcatccatg aatgtccaga ctacaaaacc     240
gggggcccca actcctgcta ctttagcaag aagcacacct ccatatggaa gatgtacgtc     300
atcacagtaa cgccatcaa ccagatggga atcagttcct cggatccact ttatgtgcac      360
gtgacttaca tagttgaacc agagcctcct gcaaacctga ctttggaatt aaaacatcca     420
gaagatagaa aaccatatct atggataaaa tggtctccac ccaccatgac tgatgtaaaa     480
tctggttggt tcattatcca gtacgaaatt cgattaaaac ctgagaaagc aactgattgg     540
gagactcatt ttactctgaa gcaaactcag cttaagattt caacttata tccaggacaa      600 aaataccttg tgcagattcg ctgcaagcca gaccatggat actggagtga gtggagccca     660
gagagctcca tccagatacc taatgacttc ccagtgaagg acacaagcat gtggatcttt     720
gtggccatcc tttctgctgt catctgtttg attatggtct gggcagtggc tttgaagggc     780
tatagcatgg tgacctgcat cctcccacca gttccagggc caaaaataaa aggatttgat     840
gttcatctgc tggagaaggg caagtccgaa gaacttctgc gagctctgga aagccaagac     900 ttcccccca cttctgactg cgaggacttg ctgatggagt tcatagaggt agatgactgt      960
gaggaccagc agctgatgcc acgcccctcc aaagaacaca cggagcaagg cgtgaagccc     1020
atgcacctgg atcttgacag tgactctggc cggggcagct gcgacagccc ttcgctcttg     1080
tctgaaaagt gtgatgaacc tcaggcccat ccctccaagt tccatactcc cgagggccct     1140
gagaagctgg agaatccgga acaaaacctt acatgtctcc aggcccctca gagcacaagc     1200
gtggaaggca aaatccccta ttttctggcc aatggaccca atcttccac atggcctttc      1260 ccgcagcccc ccagcctata cagccccaga tattcttacc acaacattgc tgacgtgtgt     1320
gagctggccc tgggcatggc cggcaccaca gccacttcgc tggaccaaac agaccaacat     1380
gct                                                                  1383

<210> SEQ ID NO 6
<211> LENGTH: 357
<212> TYPE: DNA
<213> ORGANISM: Bos taurus
```

<400> SEQUENCE: 6

```
aaagcctcaa aaaccattga aactggcagg gaaggaaagg caaccaagca gagggagtca    60
gaaggctgca gttccaagcc tgaccaagac acggtgtggc cacgacccca agacaaaacc   120
cccttgatct ctgctaaacc cttggaatac gtggagatcc acaaggtcag ccaagatgga   180
gtgctggctc tgttcccaaa acaaaacgag aagtttggcg cccctgaagc cagcaaggag   240
tactcaaagg tgtcccgggt gacagatagc aacatcctgg tattggtgcc ggatccgcaa   300
gcgcaaaacc tgactctgtt agaagaacca gccaagaagg ccccgccagc cctgcca      357
```

<210> SEQ ID NO 7
<211> LENGTH: 581
<212> TYPE: PRT
<213> ORGANISM: Bos taurus
<220> FEATURE:
<221> NAME/KEY: MISC_FEATURE
<222> LOCATION: (461)..(461)
<223> OTHER INFORMATION: Xaa can either be alanine or valine

<400> SEQUENCE: 7

```
Met Lys Glu Asn Ala Ala Ser Arg Val Val Phe Ile Leu Leu Leu Phe
1               5                   10                  15

Leu Ser Val Ser Leu Leu Asn Gly Gln Ser Pro Pro Glu Lys Pro Lys
            20                  25                  30

Leu Val Lys Cys Arg Ser Pro Gly Lys Glu Thr Phe Thr Cys Trp Trp
        35                  40                  45

Glu Pro Gly Ala Asp Gly Gly Leu Pro Thr Asn Tyr Thr Leu Thr Tyr
    50                  55                  60

His Lys Glu Gly Glu Thr Leu Ile His Glu Cys Pro Asp Tyr Lys Thr
65                  70                  75                  80

Gly Gly Pro Asn Ser Cys Tyr Phe Ser Lys Lys His Thr Ser Ile Trp
                85                  90                  95

Lys Met Tyr Val Ile Thr Val Asn Ala Ile Asn Gln Met Gly Ile Ser
            100                 105                 110

Ser Ser Asp Pro Leu Tyr Val His Val Thr Tyr Ile Val Glu Pro Glu
        115                 120                 125

Pro Pro Ala Asn Leu Thr Leu Glu Leu Lys His Pro Glu Asp Arg Lys
    130                 135                 140

Pro Tyr Leu Trp Ile Lys Trp Ser Pro Pro Thr Met Thr Asp Val Lys
145                 150                 155                 160

Ser Gly Trp Phe Ile Ile Gln Tyr Glu Ile Arg Leu Lys Pro Glu Lys
                165                 170                 175

Ala Thr Asp Trp Glu Thr His Phe Thr Leu Lys Gln Thr Gln Leu Lys
            180                 185                 190

Ile Phe Asn Leu Tyr Pro Gly Gln Lys Tyr Leu Val Gln Ile Arg Cys
        195                 200                 205

Lys Pro Asp His Gly Tyr Trp Ser Glu Trp Ser Pro Glu Ser Ser Ile
    210                 215                 220

Gln Ile Pro Asn Asp Phe Pro Val Lys Asp Thr Ser Met Trp Ile Phe
225                 230                 235                 240

Val Ala Ile Leu Ser Ala Val Ile Cys Leu Ile Met Val Trp Ala Val
                245                 250                 255

Ala Leu Lys Gly Tyr Ser Met Val Thr Cys Ile Leu Pro Pro Val Pro
            260                 265                 270

Gly Pro Lys Ile Lys Gly Phe Asp Val His Leu Leu Glu Lys Gly Lys
```

```
            275                 280                 285
Ser Glu Glu Leu Leu Arg Ala Leu Glu Ser Gln Asp Phe Pro Pro Thr
290                 295                 300

Ser Asp Cys Glu Asp Leu Leu Met Glu Phe Ile Glu Val Asp Asp Cys
305                 310                 315                 320

Glu Asp Gln Gln Leu Met Pro Arg Pro Ser Lys Glu His Thr Glu Gln
                325                 330                 335

Gly Val Lys Pro Met His Leu Asp Leu Asp Ser Asp Ser Gly Arg Gly
            340                 345                 350

Ser Cys Asp Ser Pro Ser Leu Leu Ser Glu Lys Cys Asp Glu Pro Gln
        355                 360                 365

Ala His Pro Ser Lys Phe His Thr Pro Glu Gly Pro Glu Lys Leu Glu
    370                 375                 380

Asn Pro Glu Thr Asn Leu Thr Cys Leu Gln Ala Pro Gln Ser Thr Ser
385                 390                 395                 400

Val Glu Gly Lys Ile Pro Tyr Phe Leu Ala Asn Gly Pro Lys Ser Ser
                405                 410                 415

Thr Trp Pro Phe Pro Gln Pro Pro Ser Leu Tyr Ser Pro Arg Tyr Ser
                420                 425                 430

Tyr His Asn Ile Ala Asp Val Cys Glu Leu Ala Leu Gly Met Ala Gly
            435                 440                 445

Thr Thr Ala Thr Ser Leu Asp Gln Thr Asp Gln His Xaa Leu Lys Ala
        450                 455                 460

Ser Lys Thr Ile Glu Thr Gly Arg Glu Gly Lys Ala Thr Lys Gln Arg
465                 470                 475                 480

Glu Ser Glu Gly Cys Ser Ser Lys Pro Asp Gln Asp Thr Val Trp Pro
                485                 490                 495

Arg Pro Gln Asp Lys Thr Pro Leu Ile Ser Ala Lys Pro Leu Glu Tyr
            500                 505                 510

Val Glu Ile His Lys Val Ser Gln Asp Gly Val Leu Ala Leu Phe Pro
        515                 520                 525

Lys Gln Asn Glu Lys Phe Gly Ala Pro Glu Ala Ser Lys Glu Tyr Ser
    530                 535                 540

Lys Val Ser Arg Val Thr Asp Ser Asn Ile Leu Val Leu Val Pro Asp
545                 550                 555                 560

Pro Gln Ala Gln Asn Leu Thr Leu Leu Glu Glu Pro Ala Lys Lys Ala
                565                 570                 575

Pro Pro Ala Leu Pro
            580

<210> SEQ ID NO 8
<211> LENGTH: 390
<212> TYPE: PRT
<213> ORGANISM: Bos taurus

<400> SEQUENCE: 8

Met Lys Glu Asn Ala Ala Ser Arg Val Val Phe Ile Leu Leu Leu Phe
1               5                   10                  15

Leu Ser Val Ser Leu Leu Asn Gly Gln Ser Pro Pro Glu Lys Pro Lys
            20                  25                  30

Leu Val Lys Cys Arg Ser Pro Gly Lys Glu Thr Phe Thr Cys Trp Trp
        35                  40                  45

Glu Pro Gly Ala Asp Gly Gly Leu Pro Thr Asn Tyr Thr Leu Thr Tyr
    50                  55                  60
```

His Lys Glu Gly Glu Thr Leu Ile His Glu Cys Pro Asp Tyr Lys Thr
 65                  70                  75                  80

Gly Gly Pro Asn Ser Cys Tyr Phe Ser Lys Lys His Thr Ser Ile Trp
                 85                  90                  95

Lys Met Tyr Val Ile Thr Val Asn Ala Ile Asn Gln Met Gly Ile Ser
            100                 105                 110

Ser Ser Asp Pro Leu Tyr Val His Val Thr Tyr Ile Val Glu Pro Glu
        115                 120                 125

Pro Pro Ala Asn Leu Thr Leu Glu Leu Lys His Pro Glu Asp Arg Lys
130                 135                 140

Pro Tyr Leu Trp Ile Lys Trp Ser Pro Pro Thr Met Thr Asp Val Lys
145                 150                 155                 160

Ser Gly Trp Phe Ile Ile Gln Tyr Glu Ile Arg Leu Lys Pro Glu Lys
                165                 170                 175

Ala Thr Asp Trp Glu Thr His Phe Thr Leu Lys Gln Thr Gln Leu Lys
            180                 185                 190

Ile Phe Asn Leu Tyr Pro Gly Gln Lys Tyr Leu Val Gln Ile Arg Cys
        195                 200                 205

Lys Pro Asp His Gly Tyr Trp Ser Glu Trp Ser Pro Glu Ser Ser Ile
210                 215                 220

Gln Ile Pro Asn Asp Phe Pro Val Lys Asp Thr Ser Met Trp Ile Phe
225                 230                 235                 240

Val Ala Ile Leu Ser Ala Val Ile Cys Leu Ile Met Val Trp Ala Val
                245                 250                 255

Ala Leu Lys Gly Tyr Ser Met Val Thr Cys Ile Leu Pro Pro Val Pro
            260                 265                 270

Gly Pro Lys Ile Lys Gly Phe Asp Val His Leu Leu Glu Lys Gly Lys
        275                 280                 285

Ser Glu Glu Leu Leu Arg Ala Leu Glu Ser Gln Asp Phe Pro Pro Thr
290                 295                 300

Ser Asp Cys Glu Asp Leu Leu Met Glu Phe Ile Glu Val Asp Asp Cys
305                 310                 315                 320

Glu Asp Gln Gln Leu Met Pro Arg Pro Ser Lys Glu His Thr Glu Gln
                325                 330                 335

Gly Val Lys Pro Met His Leu Asp Leu Asp Ser Asp Ser Gly Arg Gly
            340                 345                 350

Ser Cys Asp Ser Pro Ser Leu Leu Ser Glu Lys Cys Asp Glu Pro Gln
        355                 360                 365

Ala His Pro Ser Lys Phe His Thr Pro Glu Gly Pro Glu Lys Leu Glu
370                 375                 380

Asn Pro Glu Thr Asn Leu
385                 390

<210> SEQ ID NO 9
<211> LENGTH: 461
<212> TYPE: PRT
<213> ORGANISM: Bos taurus

<400> SEQUENCE: 9

Met Lys Glu Asn Ala Ala Ser Arg Val Val Phe Ile Leu Leu Leu Phe
1               5                   10                  15

Leu Ser Val Ser Leu Leu Asn Gly Gln Ser Pro Pro Glu Lys Pro Lys
            20                  25                  30

Leu Val Lys Cys Arg Ser Pro Gly Lys Glu Thr Phe Thr Cys Trp Trp
        35                  40                  45

```
Glu Pro Gly Ala Asp Gly Gly Leu Pro Thr Asn Tyr Thr Leu Thr Tyr
 50                  55                  60

His Lys Glu Gly Glu Thr Leu Ile His Glu Cys Pro Asp Tyr Lys Thr
 65                      70                  75                  80

Gly Gly Pro Asn Ser Cys Tyr Phe Ser Lys Lys His Thr Ser Ile Trp
                 85                  90                  95

Lys Met Tyr Val Ile Thr Val Asn Ala Ile Asn Gln Met Gly Ile Ser
                100                 105                 110

Ser Ser Asp Pro Leu Tyr Val His Val Thr Tyr Ile Val Glu Pro Glu
            115                 120                 125

Pro Pro Ala Asn Leu Thr Leu Glu Leu Lys His Pro Glu Asp Arg Lys
130                 135                 140

Pro Tyr Leu Trp Ile Lys Trp Ser Pro Pro Thr Met Thr Asp Val Lys
145                 150                 155                 160

Ser Gly Trp Phe Ile Ile Gln Tyr Glu Ile Arg Leu Lys Pro Glu Lys
                165                 170                 175

Ala Thr Asp Trp Glu Thr His Phe Thr Leu Lys Gln Thr Gln Leu Lys
            180                 185                 190

Ile Phe Asn Leu Tyr Pro Gly Gln Lys Tyr Leu Val Gln Ile Arg Cys
        195                 200                 205

Lys Pro Asp His Gly Tyr Trp Ser Glu Trp Ser Pro Glu Ser Ser Ile
        210                 215                 220

Gln Ile Pro Asn Asp Phe Pro Val Lys Asp Thr Ser Met Trp Ile Phe
225                 230                 235                 240

Val Ala Ile Leu Ser Ala Val Ile Cys Leu Ile Met Val Trp Ala Val
                245                 250                 255

Ala Leu Lys Gly Tyr Ser Met Val Thr Cys Ile Leu Pro Pro Val Pro
            260                 265                 270

Gly Pro Lys Ile Lys Gly Phe Asp Val His Leu Leu Glu Lys Gly Lys
        275                 280                 285

Ser Glu Glu Leu Leu Arg Ala Leu Glu Ser Gln Asp Phe Pro Pro Thr
290                 295                 300

Ser Asp Cys Glu Asp Leu Leu Met Glu Phe Ile Glu Val Asp Asp Cys
305                 310                 315                 320

Glu Asp Gln Gln Leu Met Pro Arg Pro Ser Lys Glu His Thr Glu Gln
                325                 330                 335

Gly Val Lys Pro Met His Leu Asp Leu Asp Ser Asp Ser Gly Arg Gly
            340                 345                 350

Ser Cys Asp Ser Pro Ser Leu Leu Ser Glu Lys Cys Asp Glu Pro Gln
        355                 360                 365

Ala His Pro Ser Lys Phe His Thr Pro Glu Gly Pro Glu Lys Leu Glu
370                 375                 380

Asn Pro Glu Thr Asn Leu Thr Cys Leu Gln Ala Pro Gln Ser Thr Ser
385                 390                 395                 400

Val Glu Gly Lys Ile Pro Tyr Phe Leu Ala Asn Gly Pro Lys Ser Ser
                405                 410                 415

Thr Trp Pro Phe Pro Gln Pro Ser Leu Tyr Ser Pro Arg Tyr Ser
            420                 425                 430

Tyr His Asn Ile Ala Asp Val Cys Glu Leu Ala Leu Gly Met Ala Gly
        435                 440                 445

Thr Thr Ala Thr Ser Leu Asp Gln Thr Asp Gln His Val
450                 455                 460
```

<210> SEQ ID NO 10
<211> LENGTH: 461
<212> TYPE: PRT
<213> ORGANISM: Bos taurus

<400> SEQUENCE: 10

```
Met Lys Glu Asn Ala Ala Ser Arg Val Val Phe Ile Leu Leu Leu Phe
1               5                   10                  15

Leu Ser Val Ser Leu Leu Asn Gly Gln Ser Pro Pro Glu Lys Pro Lys
            20                  25                  30

Leu Val Lys Cys Arg Ser Pro Gly Lys Glu Thr Phe Thr Cys Trp Trp
        35                  40                  45

Glu Pro Gly Ala Asp Gly Gly Leu Pro Thr Asn Tyr Thr Leu Thr Tyr
    50                  55                  60

His Lys Glu Gly Glu Thr Leu Ile His Glu Cys Pro Asp Tyr Lys Thr
65                  70                  75                  80

Gly Gly Pro Asn Ser Cys Tyr Phe Ser Lys Lys His Thr Ser Ile Trp
                85                  90                  95

Lys Met Tyr Val Ile Thr Val Asn Ala Ile Asn Gln Met Gly Ile Ser
            100                 105                 110

Ser Ser Asp Pro Leu Tyr Val His Val Thr Tyr Ile Val Glu Pro Glu
        115                 120                 125

Pro Pro Ala Asn Leu Thr Leu Glu Leu Lys His Pro Glu Asp Arg Lys
    130                 135                 140

Pro Tyr Leu Trp Ile Lys Trp Ser Pro Pro Thr Met Thr Asp Val Lys
145                 150                 155                 160

Ser Gly Trp Phe Ile Ile Gln Tyr Glu Ile Arg Leu Lys Pro Glu Lys
                165                 170                 175

Ala Thr Asp Trp Glu Thr His Phe Thr Leu Lys Gln Thr Gln Leu Lys
            180                 185                 190

Ile Phe Asn Leu Tyr Pro Gly Gln Lys Tyr Leu Val Gln Ile Arg Cys
        195                 200                 205

Lys Pro Asp His Gly Tyr Trp Ser Glu Trp Ser Pro Glu Ser Ser Ile
    210                 215                 220

Gln Ile Pro Asn Asp Phe Pro Val Lys Asp Thr Ser Met Trp Ile Phe
225                 230                 235                 240

Val Ala Ile Leu Ser Ala Val Ile Cys Leu Ile Met Val Trp Ala Val
                245                 250                 255

Ala Leu Lys Gly Tyr Ser Met Val Thr Cys Ile Leu Pro Pro Val Pro
            260                 265                 270

Gly Pro Lys Ile Lys Gly Phe Asp Val His Leu Leu Glu Lys Gly Lys
        275                 280                 285

Ser Glu Glu Leu Leu Arg Ala Leu Glu Ser Gln Asp Phe Pro Pro Thr
    290                 295                 300

Ser Asp Cys Glu Asp Leu Leu Met Glu Phe Ile Glu Val Asp Asp Cys
305                 310                 315                 320

Glu Asp Gln Gln Leu Met Pro Arg Pro Ser Lys Glu His Thr Glu Gln
                325                 330                 335

Gly Val Lys Pro Met His Leu Asp Leu Asp Ser Asp Ser Gly Arg Gly
            340                 345                 350

Ser Cys Asp Ser Pro Ser Leu Leu Ser Glu Lys Cys Asp Glu Pro Gln
        355                 360                 365

Ala His Pro Ser Lys Phe His Thr Pro Glu Gly Pro Glu Lys Leu Glu
    370                 375                 380
```

```
Asn Pro Glu Thr Asn Leu Thr Cys Leu Gln Ala Pro Gln Ser Thr Ser
385                 390                 395                 400

Val Glu Gly Lys Ile Pro Tyr Phe Leu Ala Asn Gly Pro Lys Ser Ser
            405                 410                 415

Thr Trp Pro Phe Pro Gln Pro Pro Ser Leu Tyr Ser Pro Arg Tyr Ser
        420                 425                 430

Tyr His Asn Ile Ala Asp Val Cys Glu Leu Ala Leu Gly Met Ala Gly
            435                 440                 445

Thr Thr Ala Thr Ser Leu Asp Gln Thr Asp Gln His Ala
        450                 455                 460

<210> SEQ ID NO 11
<211> LENGTH: 191
<212> TYPE: PRT
<213> ORGANISM: Bos taurus
<220> FEATURE:
<221> NAME/KEY: MISC_FEATURE
<222> LOCATION: (71)..(71)
<223> OTHER INFORMATION: Xaa can either be alanine or valine

<400> SEQUENCE: 11

Thr Cys Leu Gln Ala Pro Gln Ser Thr Ser Val Glu Gly Lys Ile Pro
1               5                   10                  15

Tyr Phe Leu Ala Asn Gly Pro Lys Ser Ser Thr Trp Pro Phe Pro Gln
            20                  25                  30

Pro Pro Ser Leu Tyr Ser Pro Arg Tyr Ser Tyr His Asn Ile Ala Asp
        35                  40                  45

Val Cys Glu Leu Ala Leu Gly Met Ala Gly Thr Thr Ala Thr Ser Leu
50                  55                  60

Asp Gln Thr Asp Gln His Xaa Leu Lys Ala Ser Lys Thr Ile Glu Thr
65                  70                  75                  80

Gly Arg Glu Gly Lys Ala Thr Lys Gln Arg Glu Ser Glu Gly Cys Ser
            85                  90                  95

Ser Lys Pro Asp Gln Asp Thr Val Trp Pro Arg Pro Gln Asp Lys Thr
        100                 105                 110

Pro Leu Ile Ser Ala Lys Pro Leu Glu Tyr Val Glu Ile His Lys Val
    115                 120                 125

Ser Gln Asp Gly Val Leu Ala Leu Phe Pro Lys Gln Asn Glu Lys Phe
130                 135                 140

Gly Ala Pro Glu Ala Ser Lys Glu Tyr Ser Lys Val Ser Arg Val Thr
145                 150                 155                 160

Asp Ser Asn Ile Leu Val Leu Val Pro Asp Pro Gln Ala Gln Asn Leu
                165                 170                 175

Thr Leu Leu Glu Glu Pro Ala Lys Lys Ala Pro Pro Ala Leu Pro
            180                 185                 190

<210> SEQ ID NO 12
<211> LENGTH: 119
<212> TYPE: PRT
<213> ORGANISM: Bos taurus

<400> SEQUENCE: 12

Lys Ala Ser Lys Thr Ile Glu Thr Gly Arg Glu Gly Lys Ala Thr Lys
1               5                   10                  15

Gln Arg Glu Ser Glu Gly Cys Ser Ser Lys Pro Asp Gln Asp Thr Val
            20                  25                  30

Trp Pro Arg Pro Gln Asp Lys Thr Pro Leu Ile Ser Ala Lys Pro Leu
```

|  | 35 | 40 | 45 |  |
|---|---|---|---|---|

Glu Tyr Val Glu Ile His Lys Val Ser Gln Asp Gly Val Leu Ala Leu
     50                      55                        60

Phe Pro Lys Gln Asn Glu Lys Phe Gly Ala Pro Glu Ala Ser Lys Glu
65                      70                      75                      80

Tyr Ser Lys Val Ser Arg Val Thr Asp Ser Asn Ile Leu Val Leu Val
                  85                      90                      95

Pro Asp Pro Gln Ala Gln Asn Leu Thr Leu Leu Glu Glu Pro Ala Lys
         100                    105                    110

Lys Ala Pro Pro Ala Leu Pro
       115

<210> SEQ ID NO 13
<211> LENGTH: 1745
<212> TYPE: DNA
<213> ORGANISM: Bos taurus

<400> SEQUENCE: 13

```
atgaaggaaa atgcagcatc tagagtggtt ttcattttgc tacttttttct cagtgtcagc      60
cttctgaatg acagtcacc tcctgaaaaa cccaagctcg ttaaatgtcg gtctcctgga     120
aaggaaacat tcacctgctg gtgggagcct ggggcagatg gaggacttcc taccaattac     180
acgctgactt accacaagga aggagaaaca ctcatccatg aatgtccaga ctacaaaacc     240
gggggcccca actcctgcta ctttagcaag aagcacacct ccatatggaa gatgtacgtc     300
atcacagtaa acgccatcaa ccagatggga atcagttcct cggatccact ttatgtgcac     360
gtgacttaca tagttgaacc agagcctcct gcaaacctga ctttggaatt aaaacatcca     420
gaagatagaa aaccatatct atggataaaa tggtctccac ccaccatgac tgatgtaaaa     480
tctggttggt tcattatcca gtacgaaatt cgattaaaac ctgagaaagc aactgattgg     540
gagactcatt ttactctgaa gcaaactcag cttaagattt caacttata tccaggacaa     600
aaatacctg tgcagattcg ctgcaagcca gaccatggaa ctggagtga gtggagccca     660
gagagctcca tccagatacc taatgacttc ccagtgaagg acacaagcat gtggatcttt     720
gtggccatcc tttctgctgt catctgtttg attatggtct gggcagtggc tttgaagggc     780
tatagcatgg tgacctgcat cctcccacca gttccagggc caaaaataaa aggatttgat     840
gttcatctgc tggagaaggg caagtccgaa gaacttctgc gagctctgga aagccaagac     900
ttcccccca cttctgactg cgaggacttg ctgatggagt tcatagaggt agatgactgt     960
gaggaccagc agctgatgcc acgccctcc aaagaacaca cggagcaagg cgtgaagccc    1020
atgcacctgg atcttgacag tgactctggc cggggcagct gcgacagccc ttcgctcttg    1080
tctgaaaagt gtgatgaacc tcaggcccat ccctccaagt tccatactcc cgagggcccct    1140
gagaagctgg agaatccgga acaaaacctt acatgtctcc aggcccctca gagcacaagc    1200
gtggaaggca aaatcccta ttttctggcc aatggaccca atcttccac atggcctttc    1260
ccgcagcccc ccagcctata cagccccaga tattcttacc acaacattgc tgacgtgtgt    1320
gagctggccc tgggcatggc cggcaccaca gccacttcgc tggaccaaac agaccaacat    1380
gtttaaaagc ctcaaaaacc attgaaactg cagggaagg aaaggcaacc aagcagaggg    1440
agtcagaagg ctgcagttcc aagcctgacc aagacacggt gtggccacga ccccaagaca    1500
aaacccccctt gatctctgct aaaccccttgg aatacgtgga gatccacaag gtcagccaag    1560
atggagtgct ggctctgttc ccaaaaacaaa acgagaagtt tggcgcccct gaagccagca    1620
```

```
aggagtactc aaaggtgtcc cgggtgacag atagcaacat cctggtattg gtgccggatc    1680
cgcaagcgca aaacctgact ctgttagaag aaccagccaa gaaggcccccg ccagccctgc   1740 catag                                                                1745
```

MATERIALS AND METHODS FOR PRODUCING ANIMALS WITH SHORT HAIR

CROSS-REFERENCE TO RELATED APPLICATION

This application claims the priority benefit of U.S. Provisional Application Ser. No. 62/054,169, filed Sep. 23, 2014, which is incorporated herein by reference in its entirety.

The Sequence Listing for this application is labeled SEQ-LIST-9-18-15-ST25.txt which was created on Sep. 18, 2015 and is 33 KB. The entire content of the sequence listing is incorporated herein by reference in its entirety.

BACKGROUND OF THE INVENTION

In a variety of circumstances it is desirable for animals to have coats with short hair. This is particularly useful in relieving heat stress in some animals. There are also instances when short hair is preferred for cosmetic and/or allergenic reasons.

Heat tolerance is an important trait in large livestock, particularly cattle. Heat kills thousands of cattle per year in the United States, reduces performance of cattle and prevents the highest performance breeds from being used in hot climates. One method for reducing heat stress in cattle is to shorten hair. In cattle, a short-haired coat is referred to as a 'slick' coat, the associated gene is called the SLICK gene, and the phenotype of a short-haired coat is called "slick phenotype".

Some cattle producers shave their cattle in the summer to improve heat tolerance; however, this method is extremely labor intensive, expensive and impractical for large herds. The Slick phenotype is found naturally in some cattle breeds of West African extraction, including Senepol, Carora, and Romosinuano; however, these breeds otherwise have modest performance and carcass qualities that limit their utility in the cattle industry.

The genetic basis for slick phenotype was identified as a single gene dominant (Olson et al. (2003), J Anim Sci.; 81(1):80-90). Traditional linkage analysis located the responsible gene to a 5 million base-pair region of cattle chromosome 20 (Mariasegaram et al. (2007), Anim Genet.; 38(1):54-59). The region was further narrowed using a genome wide associational study (GWAS) study (Huson et al. (2014), Front Genet.; April 29, Vol. 5:101). However, the narrower region contained few genes, none of which contained a mutation. Therefore, the narrowing was probably an error.

The ability to maintain homeostasis under heat stress is particularly important for cattle in subtropical and tropical regions. Although variation in heat tolerance among breeds has been studied for many years, relatively few efforts have been directed toward elucidating the mode of inheritance involved in heat tolerance. Variation in body temperature under heat stress has been studied in Australia and has been shown to have a low to moderate heritability (Turner, 1982; 1984; Mackinnon et al., 1991; Burrow, 2001). Also, Senepol cattle have been reported to be equal in heat tolerance to Brahman cattle (Hammond and Olson, 1994; Hammond et al., 1996) and Senepol F1 crossbreds with temperate breeds show heat tolerance comparable to those of Brahman and Brahman crossbreds (Hammond and Olson, 1994; Hammond et al., 1996; 1998).

Until now it was not known what mutation was responsible for the slick coat phenotype.

BRIEF SUMMARY OF THE INVENTION

The subject invention provides materials and methods for producing animals with short hair length. In a preferred embodiment, this is accomplished by altering in the animal the nucleotide sequence that encodes the prolactin receptor (PRLR) protein such that a truncated version of the protein is produced. Advantageously, and surprisingly, the truncated protein produced according to the subject invention retains lactogenic functionality, but causes the animal to have a short-hair coat.

In one embodiment, the subject invention provides polynucleotide sequences that encode truncated PRLR proteins. The polynucleotide sequences may be missing nucleotides for the truncated C-terminus or, if the nucleotides are present, they are out of the reading frame with the nucleotides that encode the N-terminus.

In a further embodiment, the current invention provides a method for producing an animal with short hair wherein the method comprises, expressing in an animal, a truncated PRLR protein, having an amino acid sequence that provides the lactogenic function but does not contain amino acids from the C-terminus of the wild type protein that are associated with a longer hair coat.

In a specific embodiment the subject invention provides genetically engineered cattle having, within their genome, a polynucleotide (e.g. SEQ ID NO: 3) that encodes a lactogenic fragment of the PRLR protein but which lacks nucleotides (e.g. SEQ ID NO: 6) that encodes the amino acids that result in a long coat, or at least lack a portion thereof. Also provided are genetically engineered cattle in which one or both copies of the PRLR genes are mutated, or truncated, such that the cattle express a truncated *B. taurus* PRLR protein and exhibit the short hair coat phenotype.

Advantageously, the identification of the SLICK gene as affecting coat length and, thus, heat stress, in animals makes it possible to engineer this trait into temperate breeds thereby increasing productivity of cattle in warm climates. In accordance with the subject invention, the fertility of dairy cows through increased embryo survival and greater milk production during periods of heat stress can be achieved. Incorporation of slick hair into temperate bovid breeds allows them to be raised successfully under conditions with greater heat stress than was previously possible.

BRIEF DESCRIPTION OF THE DRAWING

FIG. 1 shows the mutation that results in the truncation of prolactin receptor (PRLR) protein in cattle. Deletion of C (cytosine at position 1382 of SEQ ID NO: 2) from the wild type sequence causes the mutation of alanine 461 to valine and converts the following codon into a stop codon thereby producing PRLR of 461 amino acids. This mutation is represented as A461VfsX1, i.e., alanine (A) is the first amino acid changed, it is in position 461, it makes valine (V) instead, and the length of the shift frame is 1, including the stop codon (X).

BRIEF DESCRIPTION OF SEQUENCES

SEQ ID NO: 1 is the full length mRNA sequence of cattle (*Bos taurus*) PRLR.

SEQ ID NO: 2 is the nucleotide sequence encoding full length/wild type *B. taurus* PRLR.

SEQ ID NO: 3 is a nucleotide sequence encoding a minimal 390 amino acid portion of the *B. taurus* PRLR protein that retains lactogenic activity and produces slick phenotype. SEQ ID NO: 4 is an example of a nucleotide sequence encoding mutant/truncated *B. taurus* PRLR protein. Specifically, this is the sequence of the protein coding portion of the mutant mRNA of *Bos taurus* PRLR corresponding to the A461VfsX1 mutant.

SEQ ID NO: 5 is an example of the nucleotide sequence encoding a truncated *B. taurus* PRLR protein. Specifically, this is the sequence of mRNA coding for a truncated *Bos taurus* PRLR containing amino acids 1-461.

SEQ ID NO: 6 provides the polynucleotide sequence not present (in frame) in the nucleotide encoding the minimal mutant/truncated *B. taurus* PRLR protein. This sequence, or a fragment thereof, can be present in the nucleotide encoding the mutant/truncated *B. taurus* PRLR protein; however, this sequence or a fragment thereof is either not present in the protein reading frame with the nucleotide encoding the mutant/truncated *B. taurus* LRLR protein, or it encodes sufficiently few amino acids such that the slick coat phenotype occurs SEQ ID NO: 7 is the amino acid sequence of the full length *B. taurus* PRLR.

SEQ ID NO: 8 is the sequence for a 390 amino acid minimal portion of *B. taurus* PRLR protein required for milk-production, and which provides slick phenotype.

SEQ ID NO: 9 is an amino acid sequence of an example of mutated/truncated *B. taurus* PRLR protein.

SEQ ID NO: 10 is an amino acid sequence of an example of a truncated *B. taurus* PRLR protein.

SEQ ID NO: 11 is an amino acid sequence of the portion of *B. taurus* PRLR protein not present in a truncated *B. taurus* PRLR protein (amino acids 391 to 581 of the full length PRLR protein).

SEQ ID NO: 12 is the amino sequence encoded by the nucleotide sequence not present (in frame) in a truncated *B. taurus* PRLR protein.

SEQ ID NO: 13 is the mRNA sequence of the A461VfsX1 mutant of *B. taurus* PRLR.

DETAILED DISCLOSURE OF THE INVENTION

The subject invention provides materials and methods for producing animals with short hair length. In a preferred embodiment, this is accomplished by altering in the animal the nucleotide sequence that encodes the prolactin receptor (PRLR) protein such that a truncated version of the protein is produced. Advantageously, and surprisingly, the truncated protein produced according to the subject invention retains lactogenic functionality, but causes the animal to have a short-hair coat.

Thus, in one embodiment, the subject invention provides materials and methods to, for example, improve heat tolerance in an animal by conferring upon the animal a short haired (slick) coat. In preferred embodiments specifically exemplified herein, the animals are bovids.

Specifically exemplified herein are cattle that express a PRLR protein that confers milk producing capability on the cattle but also causes a short hair phenotype. In a preferred embodiment, the PRLR protein comprises the 390 N-terminus amino acids of the 581 amino acid wild-type protein. Amino acids in addition to the minimal 390 amino acid fragment can be present so long as the protein that is expressed is sufficiently truncated compared to the full length protein such that the short-hair phenotype is obtained. Preferably, the C-terminus of the full length 581 amino acid protein is truncated by at least 1, 5, 10, 15, 20, 25, 30, 35, 40, 45, 50, 55, 60, 65, 70, 75, 80, 85, 90, 95, 100, 105, 110, 115, or 120 or more amino acids.

In a specific embodiment the polynucleotide comprises nucleotides that encode the 390 amino acid portion of the PRLR protein set forth in SEQ ID NO: 8, and wherein the polynucleotide does not comprise the nucleotides that encode SEQ ID NO: 11 (amino acids 391-581). Alternatively, if all, or a portion of the nucleotides encoding SEQ ID NO: 11 is present, it is either not in the same protein reading frame as SEQ ID NO: 3 or the portion that is present and in the same reading frame as SEQ ID NO: 3 does not encode a sufficient number of amino acids to result in a normal (non-slick or non-short) coat.

The presence of the "slick coat" can be readily determined by those skilled in the art using, for example, the test set forth by Olson et al. in "Evidence of a Major Gene Influencing Hair Length and Heat Tolerance in *Bos Taurus* Cattle," J. Anim. Sci. (2003) 81:80-90, which is incorporated herein by reference in its entirety. In preferred embodiments the hair of the short coat animal is less than 50%, 40%, 30%, 20%, or even 10% the length of the hair of the animal that does not exhibit the slick hair phenotype (referred to herein as "normal" or "long-haired").

For the purpose of the current invention the term "cattle" refers to an animal belonging to *B. taurus*, *B. mutus*, and other members of the *Bos* genus. The subject invention is exemplified herein with respect to cattle; however, a person skilled in the art can practice this invention with other animals that could benefit from a short hair coat in order to improve heat tolerance, aesthetics, allergenicity, and/or cleanliness. Preferably, the animal is a non-human animal. These other animals include, but are not limited to, other bovids (particularly bovines), pigs, horses, goats, cats, mice, rats, dogs, apes, chimpanzees, and orangutans. As would be appreciated by those skilled in the art, the exact point of truncation of the PRLR portion that is needed to preserve the lactogenic function may vary from species to species as might the extent of C-terminus truncation needed to achieve the short hair coat. However, the appropriate portion of the PRLR protein to have present for a given animal can be readily determined by the skilled artisan having the benefit of the current disclosure.

In accordance with the current invention, a mutation responsible for the slick phenotype has been identified. The mutation is the A461VfsX1 mutation in the *B. Taurus* PRLR gene. The mutation results in a 120 amino acid deletion of the carboxy-terminal part of the PRLR protein.

The 120 amino acids that are deleted from the C-terminus of the PRLR protein are conserved across essentially all mammalian species. These amino acids are not essential for milk production, i.e., the PRLR missing these C-terminus amino acids can fulfill its role in the process of milk production.

SEQ ID NO: 2 is the nucleotide sequence encoding a full length *B. taurus* PRLR protein. SEQ ID NOs: 4 and 13 are nucleotide sequences encoding a mutant/truncated form of *B. taurus* PRLR protein. This specific truncated protein is encoded by the mutant PRLR gene carrying the A461VfsX1 mutation. The cattle carrying this mutation exhibit the slick phenotype.

Accordingly, the current invention provides a polynucleotide comprising a sequence of SEQ ID NO: 3, which encodes a truncated *B. taurus* PRLR protein and wherein the polynucleotide does not contain the nucleotide sequence of SEQ ID NO: 6 (or a sufficiently large portion thereof to cause a long-hair coat) in the same protein reading frame as the polynucleotide comprising SEQ ID NO: 3. For the purposes of the current invention, such polynucleotide is called a "truncated *B. taurus* PRLR polynucleotide."

For the purposes of the current invention, a first polynucleotide is in the same protein reading frame as a second polynucleotide if, when the two polynucleotides are joined (fused), the fused polynucleotide encodes a protein that contains the polypeptides independently encoded by the first and the second polynucleotides. Therefore, when the two polynucleotides are attached to each other with no intervening nucleotides, the protein reading frames of the two polynucleotides are maintained. The reading frame is not maintained between the two polynucleotides if a number of nucleotides that are not integral multiples of 3 (e.g., 1, 2, 4, 5, 7, 8, 9, 11, etc.) are inserted between the first and the second polynucleotides and/or a stop codon in the protein reading frame of the first polynucleotide is present.

Therefore, in certain specific embodiments, the truncated *B. taurus* PRLR polynucleotide of the current invention encompasses a polynucleotide comprising the sequence of SEQ ID NOs: 3, 4, or 5 that is connected with a polynucleotide comprising all or a part of SEQ ID NO: 6, wherein a number of nucleotides inserted between the polynucleotide of SEQ ID NO: 3, 4, or 5 and the polynucleotide of SEQ ID NO: 6 is not an integral multiple of 3 and/or a stop codon in the protein reading frame with the sequence of SEQ ID NOs: 3, 4, or 5 is introduced between the two polynucleotides. An example of such a polynucleotide is the polynucleotide comprising SEQ ID NO: 13, which is the nucleotide sequence of the A461VfsX1 mutant of the *B. taurus* PRLR protein and contains one nucleotide between the sequence of SEQ ID NO: 4 and part of the sequence of SEQ ID NO: 6. Alternatively, all or part of SEQ ID NO: 6 may not be present at all, so long as, if part of the sequence is present, it is not enough to cause the long-hair coat.

Thus, a truncated *B. taurus* PRLR polynucleotide can contain the sequence of SEQ ID NO: 6, or a fragment thereof; however, the sequence of SEQ ID NO: 6 or a fragment thereof, cannot encode a sufficient number of amino acids, in the protein reading frame with the sequence of the truncated *B. taurus* PRLR polynucleotide (e.g., SEQ ID NO: 3), to cause a long hair-coat.

One truncated *B. taurus* PRLR polynucleotide of the current invention encodes a truncated *B. taurus* PRLR protein, wherein the truncated protein comprises the sequence of SEQ ID NO: 8, and wherein the truncated *B. taurus* PRLR protein does not contain the sequence, or a fragment thereof sufficient to cause a long-hair coat, of SEQ ID NO: 11.

Accordingly, examples of truncated *B. taurus* PRLR proteins useful according to the current invention include fragments of a full length PRLR protein as depicted in SEQ ID NO: 7, wherein the truncated protein comprises the amino acid sequence of 1-390 to 1-461 amino acids of SEQ ID NO: 7 and the fragment does not have the sequence, or a fragment thereof, of SEQ ID NO: 11.

Table 1 provides certain examples of truncated *B. taurus* PRLR polynucleotides and truncated *B. taurus* PRLR proteins encoded by those polynucleotides. The sequence of all of the truncated *B. taurus* PRLR polynucleotides depicted in Table 1 begin at position 1 of SEQ ID NO: 4 or 5 and the sequence of the truncated *B. taurus* PRLR proteins depicted in Table 1 begin at position 1 of SEQ ID NO: 7. Various ending positions of the polynucleotides correspond to SEQ ID NO: 4 or 5 and various ending positions of amino acids correspond to SEQ ID NO: 7.

TABLE 1

| Ending nucleotide position of the truncated *B. taurus* PRLR polynucleotide | Size of truncated *B. taurus* PRLR protein encoded by the polynucleotide (number of amino acids) | Amino acid sequence of the truncated *B. taurus* PRLR protein |
|---|---|---|
| 1170 | 390 | 1-390 |
| 1173 | 391 | 1-391 |
| 1176 | 392 | 1-392 |
| 1179 | 393 | 1-393 |
| 1182 | 394 | 1-394 |
| 1185 | 395 | 1-395 |
| 1188 | 396 | 1-396 |
| 1191 | 397 | 1-397 |
| 1194 | 398 | 1-398 |
| 1197 | 399 | 1-399 |
| 1200 | 400 | 1-400 |
| 1203 | 401 | 1-401 |
| 1206 | 402 | 1-402 |
| 1209 | 403 | 1-403 |
| 1212 | 404 | 1-404 |
| 1215 | 405 | 1-405 |
| 1218 | 406 | 1-406 |
| 1221 | 407 | 1-407 |
| 1224 | 408 | 1-408 |
| 1227 | 409 | 1-409 |
| 1230 | 410 | 1-410 |
| 1233 | 411 | 1-411 |
| 1236 | 412 | 1-412 |
| 1239 | 413 | 1-413 |
| 1242 | 414 | 1-414 |
| 1245 | 415 | 1-415 |
| 1248 | 416 | 1-416 |
| 1251 | 417 | 1-417 |
| 1254 | 418 | 1-418 |
| 1257 | 419 | 1-419 |
| 1260 | 420 | 1-420 |
| 1263 | 421 | 1-421 |
| 1266 | 422 | 1-422 |
| 1269 | 423 | 1-423 |
| 1272 | 424 | 1-424 |
| 1275 | 425 | 1-425 |
| 1278 | 426 | 1-426 |
| 1281 | 427 | 1-427 |
| 1284 | 428 | 1-428 |
| 1287 | 429 | 1-429 |
| 1290 | 430 | 1-430 |
| 1293 | 431 | 1-431 |
| 1296 | 432 | 1-432 |
| 1299 | 433 | 1-433 |
| 1302 | 434 | 1-434 |
| 1305 | 435 | 1-435 |
| 1308 | 436 | 1-436 |
| 1311 | 437 | 1-437 |
| 1314 | 438 | 1-438 |
| 1317 | 439 | 1-439 |
| 1320 | 440 | 1-440 |
| 1323 | 441 | 1-441 |
| 1326 | 442 | 1-442 |
| 1329 | 443 | 1-443 |
| 1332 | 444 | 1-444 |
| 1335 | 445 | 1-445 |
| 1338 | 446 | 1-446 |
| 1341 | 447 | 1-447 |
| 1344 | 448 | 1-448 |
| 1347 | 449 | 1-449 |
| 1350 | 450 | 1-450 |
| 1353 | 451 | 1-451 |
| 1356 | 452 | 1-452 |
| 1359 | 453 | 1-453 |
| 1362 | 454 | 1-454 |
| 1365 | 455 | 1-455 |
| 1368 | 456 | 1-456 |
| 1371 | 457 | 1-457 |
| 1374 | 458 | 1-458 |
| 1377 | 459 | 1-459 |
| 1380 | 460 | 1-460 |
| 1383 | 461 | 1-461 |

Fragments larger than 461 amino acids are also within the scope of the invention, so long as they are not large enough to result in the non-slick phenotype.

The current invention also provides homologs of the truncated *B. taurus* PRLR polynucleotides and truncated *B. taurus* PRLR proteins.

For the purposes of the present invention, the term "homolog" refers to a sequence having a percentage identity with the reference sequence of between at least 70% to about 99% (inclusive). The aforementioned range of percent identity is to be taken as including, and providing written description support for, any fractional percentage, in intervals of 1%, from 70% to 99%. For example, homologous sequences can exhibit a percent identity of 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent with the reference sequences.

Typically, the percent identity is calculated over the entirety of the reference sequence. The terms "identical" or percent "identity," in the context of two or more sequences, refer to two or more sequences or subsequences that are the same or have a specified percentage of residues that are the same, when compared and aligned for maximum correspondence over a comparison window, as measured using a sequence comparison algorithm or by manual alignment and visual inspection.

The current invention also provides homologs of the truncated *B. taurus* PRLR polynucleotides and truncated *B. taurus* PRLR proteins having at least 70% to about 99% (inclusive) sequence identity with the truncated *B. taurus* PRLR polynucleotides and proteins.

Certain examples of homologs of the truncated *B. taurus* PRLR polynucleotides include polynucleotides having a sequence identity of about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent with the sequences of SEQ ID NOs: 3, 4, or 5. The homologs of the truncated *B. taurus* PRLR polynucleotides also do not contain the sequence, or a fragment thereof, sufficient to result in a long coat, of SEQ ID NO: 6 in frame with the protein reading region of the homologs.

Certain examples of homologs of the truncated *B. taurus* PRLR proteins include proteins having a sequence identity of about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent with the sequences of SEQ ID NOs: 8, 9, or 10. The homologs of the truncated *B. taurus* PRLR proteins also do not contain the sequence, or a fragment thereof, sufficient to result in a long coat, of SEQ ID NO: 11.

Nucleic acid sequences useful according to the subject invention include variants of the exemplified nucleotide sequences wherein the variants encode amino acid sequences that are identical to the sequences encoded by the exemplified polynucleotide sequences. Because of the degeneracy of the genetic code, multiple nucleic acid sequences encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are called silent mutations. One of ordinary skill will recognize that each codon in a nucleic acid (except AUG, which is ordinarily the only codon for methionine); can be modified yet still encode the same amino acid sequence. Such variant sequences having silent mutants, which encode a polypeptide of the present invention, are within the purview of the claimed invention.

Nucleic acid sequence homologies can be identified using any of the variety of sequence comparison algorithms and programs known in the art. Such algorithms and programs include, but are not limited to, TBLASTN, BLASTP, FASTA, TFASTA, and CLUSTALW (Pearson and Lipman, 1988, *Proc. Natl. Acad. Sci. USA* 85(8):2444-2448; Altschul et al., 1990, *J. Mol. Biol.* 215(3):403-410; Thompson et al., 1994, *Nucleic Acids Res.* 22(2):4673-4680; Higgins et al., 1996, *Methods Enzymol.* 266:383-402; Altschul et al., 1990, *J. Mol. Biol.* 215(3):403-410; Altschul et al., 1993, *Nature Genetics* 3:266-272). Sequence comparisons are, typically, conducted using default parameters provided by the vendor or using those parameters set forth in the above-identified references, which are hereby incorporated by reference in their entireties.

The term "about" is used in this patent application to describe some quantitative aspects of the invention, for example, concentration of an inducer or percent identity between nucleotide sequences. It should be understood that absolute accuracy is not required with respect to those aspects for the invention to operate. When the term "about" is used to describe a quantitative aspect of the invention the relevant aspect may be varied by ±10%.

A "complementary" polynucleotide sequence, as used herein, generally refers to a sequence arising from the hydrogen bonding between a particular purine and a particular pyrimidine in double-stranded nucleic acid molecules (DNA-DNA, DNA-RNA, or RNA-RNA). The major specific pairings are guanine with cytosine and adenine with thymine or uracil. A "complementary" polynucleotide sequence can also be referred to as an "antisense" polynucleotide sequence or an "antisense sequence". In various aspects of the invention, sequences are "fully complementary" to a reference sequence, which refers to sequences containing no mismatches in their base pairing.

As used herein, "vector" refers to a DNA molecule such as a plasmid, cosmid, or bacterial phage for introducing a nucleotide construct, for example, a DNA construct, into a host cell. Cloning vectors typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide antibiotic resistance. Non-limiting examples of selection antibiotics that can be used in practicing the current invention include Geneticin (G-418), mycophenolic acid, and zeocin. Additional examples of antibiotics suitable for use in the current invention are known to a skilled artisan and such embodiments are within the purview of the current invention.

The subject invention also provides detection probes (e.g., fragments of the *B. taurus* PRLR polynucleotides) for hybridization with a target sequence or an amplicon generated from the target sequence. Such a detection probe will comprise a contiguous/consecutive span of at least 8, 9, 10, 11, 12, 15, 16, 17, 18, 19, 20, 21, 22, 23, 24, 25, 26, 27, 28, 29, 30, 35, 40, 45, 50, 55, 60, 65, 70, 75, 80, 85, 90, 95, or 100 or more nucleotides of any of the *B. taurus* PRLR polynucleotides (e.g. polynucleotides described in Table 1, SEQ ID NOs: 3, 4, and 5).

Labeled probes or primers are labeled with a radioactive compound or with another type of label, e.g., 1) radioactive labels, 2) enzyme labels, 3) chemiluminescent labels, 4) fluorescent labels, or 5) magnetic labels). Alternatively, non-labeled nucleotide sequences can be used directly as probes or primers; however, the sequences are generally labeled with a radioactive element ($^{32}P$, $^{35}S$, $^{3}H$, $^{125}I$) or with a molecule such as biotin, acetylaminofluorene, digoxigenin, 5-bromo-deoxyuridine, or fluorescein to provide probes that can be used in numerous applications.

The *B. taurus* PRLR polynucleotides disclosed herein are useful in methods of expressing truncated *B. taurus* PRLR proteins in cells or in animals, for example, cattle and other bovids. This can be accomplished by transforming a cell of interest with a DNA construct comprising the *B. taurus* PRLR polynucleotide (a transgenic gene construct) and generating a transformed cell expressing truncated *B. taurus* PRLR protein.

In additional embodiments, the present invention relates to transfection vectors, expression vectors, host cells, and transgenic animals comprising the truncated *B. taurus* PRLR polynucleotide encoding a truncated PRLR protein.

In another embodiment, the present invention relates to isolated truncated *B. taurus* PRLR proteins, as well as fusion polypeptides comprising such isolated truncated *B. taurus* PRLR proteins.

Various methods disclosed herein include introducing a nucleotide (DNA) construct into a cell. The term "introducing" is used herein to mean presenting to the cell the nucleotide construct in such a manner that the construct gains access to the interior of the cell These methods do not depend on a particular method for introducing a nucleotide construct to a cell, only that the nucleotide construct gains access to the interior of the cell. Methods for introducing nucleotide constructs into cells are known in the art including, but not limited to, stable transformation methods, transient transformation methods, and virus-mediated methods.

The current invention also provides a method of using the truncated PRLR polynucleotides to genetically modify animals that do not naturally exhibit the slick phenotype to produce animals exhibiting the slick phenotype. To add slick phenotype to any breed, any mutation that causes the expression of the truncated PRLR protein can be used.

Accordingly, in one embodiment the current invention provides a method of producing a non-human mammal having a short-haired phenotype, wherein the mammal expresses a truncated PRLR protein comprising at least 1-390 amino acids of the sequence set forth in SEQ ID NO: 7 and does not contain all of the amino acids 391-581 of the sequence set forth in SEQ ID NO: 7. The method of the current invention comprises:

a) obtaining a cell capable of being developed in to a non-human mammal, and b) introducing a polynucleotide encoding the truncated PRLR protein into the cell or manipulating the genomic DNA of the cell so that the genomic DNA comprises the polynucleotide encoding the truncated PRLR protein, and c) producing the non-human mammal cell from the cell.

The polynucleotide encoding the truncated PRLR protein can comprise a sequence of SEQ ID NO: 3 or a homolog thereof having at least 90% sequence identity to the sequence of SEQ ID NO: 3 and the polynucleotide does not contain the full nucleotide sequence of SEQ ID NO: 6 or does not contain the full nucleotide sequence of SEQ ID NO: 6 in the protein reading frame of the polynucleotide of SEQ ID NO: 3. Examples of a polynucleotide that can be used in the methods of the current invention are polynucleotides comprising the sequence of SEQ ID NO: 3, 4, 5, or 13. An example of the truncated PRLR protein which provides the short hair phenotype to the non-human mammal is a protein having the sequence of SEQ ID NO: 8.

In one embodiment, the cell capable of being developed in to the non-human mammal is a totipotent cell. A totipotent cell has the ability to develop into a complete organism or differentiating into any of its cells or tissues. Non-limiting examples of totipotent cells that can be used in the methods of the current invention are stem cells, embryonic stem cells, fertilized oocytes and zygotes. Additional examples of totipotent cells that can be used according to the current invention are well known to a person of ordinary skill in the art and such embodiments are within the purview of the current invention.

In certain embodiments the non-human mammal is a bovid, cattle, pig, horse, goat, cat, mouse, sheep, rat, dog, ape, chimpanzee, or orangutan. Non-limiting examples of PRLR proteins that can be used according to the subject invention are proteins having UniProt accession numbers Q28172, Q08501, P14787, O46561, P05710, Q58DZ7, Q6JTA8, C7T4Z0, Q3HNA7, D0VFV2, C7T4V8, C7T4W1, C7T4W4, C7T4X8, Q2PBP0, B3GDH0, C7T4X9, E7BKJ5, G3UVW6, Q58DZ7, E7CHC7, E5KXH8, D3ZV73, D0VFV3, F2XX66, I7FI71, E9MW50, Q28172, F1N4H8, Q2PBN9, C7F8W7, G1DE70, S5TFK4, Q28235, O46561, Q08501, Q99JZ1, U6CXL9, P05710, F1M137, P14787, F7HIV1, Q865V4, Q6JTA8, D9IWB8, Q9XS92, and K7GKV2.

The genetically engineered animals can be produced by methodologies known in the art for making genetically engineered animals, particularly, mammals. Non-limiting examples of such technologies include producing transgenic cattle expressing the truncated *B. taurus* PRLR protein, homologous recombination to replace wild type protein in a cattle strain with the truncated protein, deletion of relevant bases in the genome of a cattle strain which would result in the production of truncated protein, or any other methodology for genome editing. Additional examples include methods involving recombinant retroviruses, pronuclear injection, sperm-mediated DNA transfer, germ cell transplantation, and nuclear transfer cloning. Even further methods of producing genetically modified mammals according to the methods of the current invention are well known to a person of ordinary skill in the art and such methods are within the purview of the claimed invention.

The term "genetically engineered cattle" as used herein encompasses transgenic cattle and cattle carrying mutations in one or both copies of PRLR gene wherein the mutation results in the expression of truncated PRLR protein.

Transgenic cattle refers to cattle expressing truncated PRLR protein via one or more copies of a truncated PRLR polynucleotide incorporated into the cattle's genome. Cattle carrying a mutation or truncation in one copy of the PRLR gene wherein the mutation or truncation results in expression of the truncated PRLR protein are called heterozygous cattle; whereas, cattle carrying mutations, or truncations, in both copies of PRLR gene, wherein the mutation results in the expression of truncated PRLR protein are called homozygous cattle.

A transgenic, homozygous or heterozygous cattle expressing truncated PRLR protein can exhibit the slick phenotype.

In one embodiment, transcription activator-like effector nucleases-mediated (TALEN-mediated) homologous recombination is used to produce the homozygous or heterozygous cattle exhibiting the slick phenotype. Examples of producing TALEN-mediated genetically engineered organisms are provided by Zu et al. (2013), TALEN-mediated precise genome modification by homologous recombination in zebrafish, Nature Methods, 10:329-331; Katsuyama et al. (2013), An efficient strategy for TALEN-mediated genome engineering in *Drosophila*, Nucleic Acids Research, Vol. 41, No. 17, e163; and Liu et al. (2014), TALEN-Mediated Gene Mutagenesis in Rhesus and Cynomolgus Monkeys, Cell Stem Cell, Vol. 14, Issue 3, pp. 323-328.

Clustered Regularly Interspaced Short Palindromic Repeats (CRISPR) and CRIPS-associated genes (CAS) system (CRISPR/CAS system) can also be used to produce the homozygous or heterozygous cattle exhibiting the slick phenotype. Examples of the use of CRISPR/CAS system to produce genetically engineered organisms, particularly mammals, are provided by Cong et al. (2013), Multiplex Genome Engineering Using CRISPR/Cas Systems, Science, Vol. 339 no. 6121 pp. 819-823 and in U.S. Pat. No. 8,795, 965.

Additional techniques of generating homozygous or heterozygous bovids and other animals are well known to a person of ordinary skill in the art and such embodiments are within the purview of the current invention.

Methods for generating transgenic animals are well known to a person of ordinary skill in the art. Transgenic gene constructs can be introduced into the germ line of cattle to make transgenic cattle. For example, one or several copies of the construct may be incorporated into the genome of a mammalian embryo by standard transgenic techniques.

Transgenic cattle can be produced by introducing transgenes encoding a truncated *B. taurus* PRLR protein into the germline of the cattle. Embryonal target cells at various developmental stages can be used to introduce transgenes. Different methods are used depending on the stage of development of the embryonal target cell. The specific line(s) of any animal used are selected for general good health, good embryo yields, good pronuclear visibility in the embryo, and good reproductive fitness.

Introduction of the transgene into the embryo can be accomplished by any means known in the art, for example, microinjection, electroporation, or lipofection. For example, but not by way of limitation, a truncated PRLR protein transgene can be introduced into an animal by microinjection of the construct into the pronuclei of the fertilized cattle egg(s), causing one or more copies of the construct to be retained in the cells of the developing cattle. Following introduction of the transgene construct into the fertilized egg, the egg may be incubated in vitro for varying amounts of time, or re-implanted into the surrogate host, or both. In vitro incubation to maturity is included. A common method is to incubate the embryos in vitro for about 1-7 days and re-implant them into the surrogate host.

The progeny of the transgenically manipulated embryos can be tested for the presence of the construct by various methods designed to identify the presence of the truncated PRLR polynucleotides. If one or more copies of the exogenous cloned construct remain stably integrated into the genome of such transgenic embryos, it is possible to establish permanent transgenic lines carrying the transgenically added construct.

Litters of transgenically altered animals can be assayed after birth for the incorporation of the construct into the genome of the offspring. Preferably, this assay is accomplished by hybridizing a probe corresponding to the DNA sequence coding for the desired truncated PRLR protein onto chromosomal material from the progeny. Those progeny found to contain at least one copy of the construct in their genome are grown to maturity.

The term zygote as used herein refers to a diploid cell that is capable of developing into a complete organism. Generally, the zygote will be comprised of an egg containing a nucleus formed, either naturally or artificially, by the fusion of two haploid nuclei from one or more gametes. Thus, the gamete nuclei must be ones that are naturally compatible, i.e., ones that result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

The number of copies of the transgene constructs that are added to the zygote is dependent upon the total amount of exogenous genetic material added and will be the amount that enables the genetic transformation to occur. Theoretically only one copy is required; however, generally, numerous copies are utilized, for example, 1,000-20,000 copies of the transgene construct are generated to ensure that one copy is functional. There will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and used in the art.

Re-implantation is accomplished using standard methods. Usually, the surrogate host is anesthetized, and the embryos are inserted into the oviduct.

Transgenic offspring of the surrogate host may be screened for the presence and/or expression of the transgene by any suitable method. Screening can be accomplished by Southern blot or Northern blot analysis, using a probe that is complementary to at least a portion of the transgene. Typically, DNA is prepared from tissue and analyzed by Southern analysis or PCR for the transgene. Alternatively, the tissues or cells believed to express the transgene at the highest levels are tested for the presence and/or expression of truncated *B. taurus* PRLR proteins, although any tissues or cell types may be used for this analysis.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout. Where it is transgenic, it may contain the same or a different transgene, or both. Alternatively, the partner may be a parental line. When in vitro fertilization is used, the fertilized embryo may be implanted into a surrogate host or incubated in vitro, or both. Using these methods, the progeny may be evaluated for the presence of the transgene using appropriate methods.

The transgenic animals produced in accordance with the present description will include exogenous genetic material. As set out above, the exogenous genetic material will, in certain embodiments, be a DNA sequence that results in the production of truncated PRLR protein. Further, in such embodiments the sequence will be attached to a transcriptional control element, e.g., a promoter, which preferably allows the expression of the transgene product in a specific type of cell which produces a transgenic animal expressing truncated PRLR protein in a tissue specific manner.

Blastocytes offer a second type of target cell for transgene introduction into cattle (and other animals). When developing transgenic cattle, a cattle embryo, is cultured in vitro to the blastocyst stage, it can be targeted for retroviral infection. Efficient infection of the blastomeres is obtained by enzymatic treatment to remove the zona pellucida (Manipulating the Mouse Embryo, Hogan eds. (Cold Spring Harbor Laboratory Press, Cold Spring Harbor, 1986). The viral vector system used to introduce the transgene is typically a replication-defective retrovirus carrying the transgene. Transfection is easily and efficiently obtained by culturing the blastomeres on a monolayer of virus-producing cells.

Alternatively, infection can be performed at a later stage. Virus or virus-producing cells can be injected into the blastocoele. Most of the founders will be mosaic for the transgene since incorporation occurs only in a subset of the cells that formed the transgenic cattle. Further, the founder may contain various retroviral insertions of the transgene at different positions in the genome which generally will segregate in the offspring. In addition, it is also possible to introduce transgenes into the germ line by intrauterine retroviral infection of the midgestation embryo.

A third type of target cell for transgene introduction is the embryonal stem cell (ES). ES cells are obtained from pre-implantation embryos cultured in vitro and fused with embryos. Transgenes can be efficiently introduced into the ES cells by DNA transfection or by retrovirus-mediated transduction. Such transformed ES cells can thereafter be combined with blastocysts from cattle. The ES cells thereafter colonize the embryo and contribute to the germ line of the resulting chimeric animal.

Also provided are transgenic bovids, and other animals, where the transgenic animal is characterized by slick phenotype. Alterations to the gene can include, deletions, mutations, or truncations that result in the production of truncated PRLR protein; or the introduction of an exogenous gene, such as one having a truncated PRLR polynucleotide; or a combination of the foregoing.

A further embodiment of the current invention provides a method of identifying whether a particular animal carries the mutant PRLR gene encoding the truncated PRLR protein. A test to identify the presence of PRLR mutation and the copy number of the mutant PRLR gene can also improve selection of embryos to be transferred in the methods of producing genetically engineered cattle (and other animals).

Examples of non-limiting molecular biology techniques that can be used to identify PRLR truncation mutant include:
(A) Mutation-specific PCR from DNA or RNA. DNA or RNA (converted to cDNA) can be isolated from the animals to be tested. Primers specific to the mutant or normal allele can be designed such that the PCR is indicative of whether the mutation exists. Based on the nucleotide sequences provided herein, a person of ordinary skill in the art can design appropriate primers for the mutation specific PCR from DNA or RNA and such embodiments are within the purview of the current invention.
(B) Restriction site. The mutation A461VfsX1 creates a new palindrome sequence in the genomic DNA-ACATGT. This palindromic sequence is not present in the native/non-mutated genome. A PCR product produced with primers that amplify the region of the genomic DNA that spans the mutation site can be cut with a restriction enzyme specific to this sequence (e.g., restriction endonuclease PciI). Ability to be cut by an endonuclease that acts on the palindromic sequence TGTACA is indicative of presence of the mutation.
(C) Direct sequencing. The region of the mutation can be PCR amplified from mRNA (which can be optionally converted to cDNA) or genomic DNA. The PCR product can be sequenced to identify the presence of the PRLR mutant gene. Based on the nucleotide sequences provided herein, a person of ordinary skill in the art can design appropriate primers sequencing DNA or RNA and such embodiments are within the purview of the current invention.
(D) Single strand conformation polymorphism (SSCP) and heteroduplex analysis tests can be designed to identify the point mutation in the DNA.
(E) Western blot using antibodies specific to the carboxy terminus of PRLR protein. Absence of a band on western blot which corresponds to the full length PRLR protein indicates the presence of the mutation and expression of truncated PRLR protein.

The current invention also provides antibodies that can be used for detection of mutants in cattle that express truncated *B. taurus* PRLR protein. These antibodies are directed to C-terminal amino regions or epitopes located in the C-terminal region of the full PRLR protein. Accordingly, the current invention provides a polypeptide consisting of a sequence of SEQ ID NO: 11 or fragments thereof. These polypeptides can be used to raise antibodies that can be used to detect mutants in cattle that express truncated *B. taurus* PRLR protein.

All patents, patent applications, provisional applications, and publications referred to or cited herein are incorporated by reference in their entirety, including all FIGURES and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:

1. A method of producing a modified bovine cell comprising:
   a) obtaining a bovine cell, wherein the genomic DNA of the bovine cell comprises a full-length wild-type prolactin receptor (PRLR) protein; and
   b) introducing a polynucleotide encoding a truncated PRLR protein into the bovine cell such that the polynucleotide is incorporated into the genome of the bovine cell to produce the modified bovine cell, wherein the truncated PRLR protein is 426 amino acids in length.

2. The method of claim 1, wherein the polynucleotide encoding the truncated PRLR protein comprises a sequence having at least 90% sequence identity to the sequence of SEQ ID NO: 3.

3. The method of claim 1, wherein the introducing the polynucleotide encoding the truncated PRLR protein into the bovine cell such that the polynucleotide is incorporated into the genome of the bovine cell is performed using a Clustered Regularly Interspaced Short Palindromic Repeats (CRISPR)/CAS system or Transcription Activator-Like Effector Nucleases (TALEN)-mediated engineering.

4. The method of claim 1, wherein the truncated PRLR protein consists of amino acids 1-426 of SEQ ID NO.: 7.

5. The method of claim 1, wherein the polynucleotide encoding the truncated PRLR protein comprises a sequence having at least 95% sequence identity to the sequence of SEQ ID NO: 3.

* * * * *